(12) United States Patent  
Negishi et al.

(10) Patent No.: US 7,125,920 B2
(45) Date of Patent: Oct. 24, 2006

(54) ULTRAVIOLET ABSORBER FOR SYNTHETIC RESIN AND SYNTHETIC RESIN COMPOSITION CONTAINING THE SAME

(75) Inventors: Yoshinori Negishi, Saitama (JP); Etsuo Tobita, Saitama (JP); Takashi Ayabe, Saitama (JP)

(73) Assignee: Asahi Denka Kogyo K.K., Tokyo (JP)

( * ) Notice: Subject to any disclaimer, the term of this patent is extended or adjusted under 35 U.S.C. 154(b) by 197 days.

(21) Appl. No.: 10/432,841

(22) PCT Filed: Apr. 8, 2002

(86) PCT No.: PCT/JP02/03479

§ 371 (c)(1),
(2), (4) Date: May 28, 2003

(87) PCT Pub. No.: WO02/081559

PCT Pub. Date: Oct. 17, 2002

(65) Prior Publication Data

US 2004/0099849 A1 May 27, 2004

(30) Foreign Application Priority Data

Apr. 6, 2001 (JP) .............................. 2001-109097
Dec. 26, 2001 (JP) .............................. 2001-394985

(51) Int. Cl.
C08K 5/3492 (2006.01)
C07D 251/24 (2006.01)
(52) U.S. Cl. ...................... 524/100; 252/403; 544/216
(58) Field of Classification Search ................ 252/403; 524/100; 544/180, 216
See application file for complete search history.

(56) References Cited

U.S. PATENT DOCUMENTS 3,118,887 A * 1/1964 Pinto et al. .................. 544/216
6,242,597 B1 * 6/2001 Gupta et al. ................. 544/216

FOREIGN PATENT DOCUMENTS

| EP | 001033243 A1 * | 6/2000 |
| JP | 04-214785 A | 8/1992 |
| JP | 05-93089 | 4/1993 |
| JP | 05-125248 | 5/1993 |
| JP | 10-17337 | 1/1998 |
| JP | 10-95974 A | 4/1998 |
| JP | 10-147577 | 6/1998 |
| JP | 2779981 | 7/1998 |
| JP | 11-181304 | 7/1999 |

(Continued)

Primary Examiner—Kriellion Sanders
(74) Attorney, Agent, or Firm—Nixon & Vanderhye PC

(57) ABSTRACT

The present invention relates to an ultraviolet absorber for synthetic resins composed of a triazine compound represented by the general formula (I) shown below

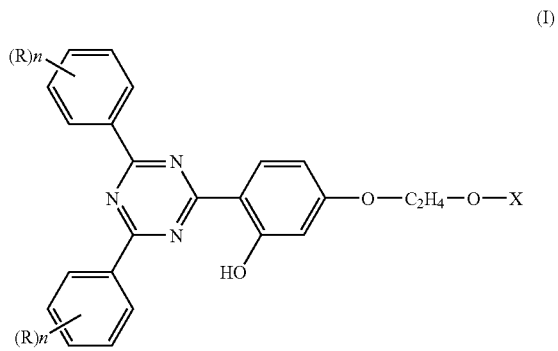

(wherein R represents an alkyl group having 1 to 4 carbon atoms, n is 0 or an integer of up to 2, and X represents a group selected from the consisting of group (a) to (d) shown below)

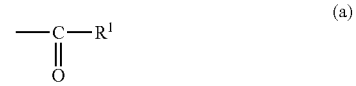

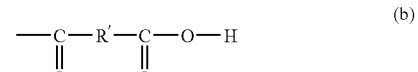

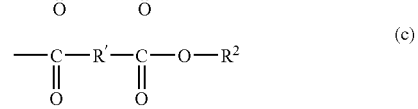

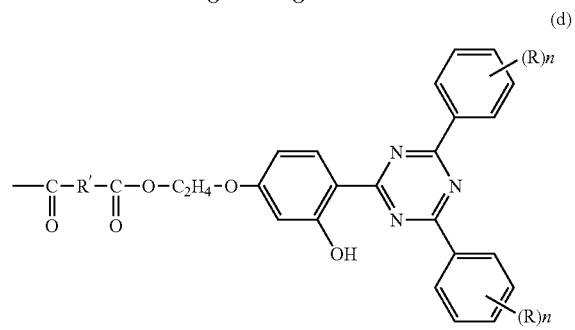

(wherein $R^1$ represents an aliphatic group having 5 to 60 carbon atoms, which is an alicyclic group, an alkyl group having an alicyclic group at the terminal or in the chain thereof, an alkyl group having a branch, or a linear alkyl group, depending on the number of carbon atoms; $R^2$ represents an alkyl group having 1 to 18 carbon atoms or a (poly)alkyleneoxyalkyl group; R' represents an aliphatic diyl group having 5 to 60 carbon atoms; R and n have the same meanings as those described in the general formula (I) above).

6 Claims, No Drawings

FOREIGN PATENT DOCUMENTS

| | | |
|---|---|---|
| JP | 2000-313051 | 11/2000 |
| JP | 2001-32171 | 2/2001 |
| JP | 2001-032171 | 6/2001 |
| JP | 2001-302926 | 10/2001 |
| JP | 2001-524473 | 12/2001 |
| WO | WO 99/26934 | 5/1999 |

* cited by examiner

ULTRAVIOLET ABSORBER FOR SYNTHETIC RESIN AND SYNTHETIC RESIN COMPOSITION CONTAINING THE SAME

TECHNICAL FIELD

The present invention relates to an ultraviolet absorber for synthetic resins that is composed of a triazine compound having a specific structure and being excellent in compatibility with synthetic resins and to a synthetic resin composition containing the ultraviolet absorber.

BACKGROUND ART

Synthetic resins typified by polyolefin resins such as polyethylene and polypropylene, polycarbonate resins, polyester resins such as polyethylene terephthalate and polybutylene terephthalate, styrene resins such as polystyrene, butadiene-styrene, ABS and ACS, polyamide resins such as nylon, polyvinyl chloride, polyphenylene ether, polymethyl methacrylate and the like are used widely in various fields as various molded articles, fibers, films and coating materials.

However, it has been known that molded articles composed exclusively of the above-mentioned synthetic resins are deteriorated by natural light, particularly by ultraviolet rays in the natural light to undergo discoloration and reduction in mechanical strength so that they cannot endure a prolonged use.

Accordingly, to prevent deterioration by light of these resins to be processed into molded articles, there have conventionally been used ultraviolet absorbers and light stabilizers either singly or in combination. Triazine compounds are known to be ultraviolet absorbers that exhibit excellent effects, which has been reported in, for example, JP 4-214785 A, JP 5-125248 A, JP 5-93089 A, JP 10-95974 A, JP 10-147577 A, JP 2779981 B, and JP 2000-313051 A.

However, the above-reported triazine compounds have insufficient compatibility and/or dispersibility with the resin component, failing to give a sufficient effect of addition. In thermoplastic resins for mold processing such as polycarbonate resins, polyolefin resins, polyester resins, this problem is particularly conspicuous. Furthermore, polyolefin resins have problems such as deterioration of transparency due to blooming or turbidity.

Therefore, an object of the present invention is to provide an ultraviolet absorber for synthetic resins that has good compatibility or dispersibility with the resin component and gives sufficient effect of addition and a synthetic resin composition containing the ultraviolet absorber.

DISCLOSURE OF THE INVENTION

As a result of extensive studies, the inventors of the present invention have found that an ultraviolet absorber for synthetic resins that is composed of a triazine compound having a specific structure has good dispersibility in synthetic resins and gives excellent weatherability thereto, thereby achieving the present invention.

That is, according to a first aspect, the present invention provides an ultraviolet absorber for synthetic resins composed of a triazine compound represented by the general formula (I) below.

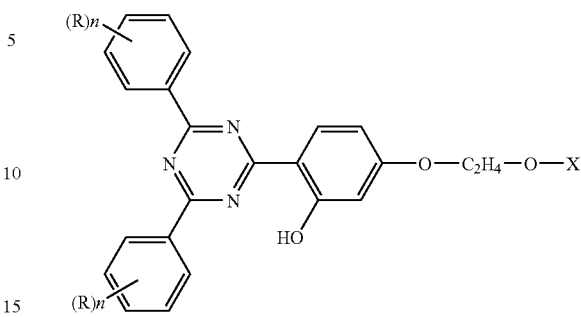

(Wherein R represents an alkyl group having 1 to 4 carbon atoms, n is 0 or an integer of up to 2, and X represents a group selected from the group consisting of (a) to (d) shown below.)

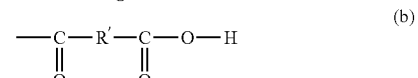

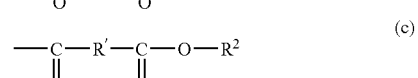

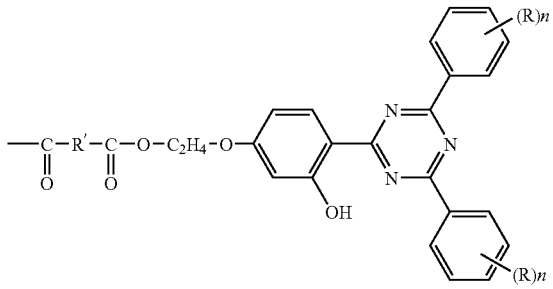

(wherein $R^1$ represents an aliphatic group having 5 to 60 carbon atoms, which is a group selected from the group consisting of an alicyclic group and an alkyl group having an alicyclic group at the terminal or in the chain thereof, when the aliphatic group has 5 to 8 carbon atoms;

a group selected from the group consisting of an alicyclic group, an alkyl group having an alicyclic group at the terminal or in the chain thereof, and an alkyl group having a branch, when the aliphatic group has 9 to 19 carbon atoms; or a group selected from the group consisting of an alicyclic group, an alkyl group having an alicyclic group at the terminal or in the chain thereof, an alkyl group having a branch, and a linear alkyl group, when the aliphatic group has 20 to 60 carbon atoms;

$R^2$ is a group selected from the group consisting of an alkyl group having 1 to 18 carbon atoms, which may be branched or may have an alicyclic group at the terminal or in the chain thereof, and a (poly)alkyleneoxyalkyl group (with the number of carbon atoms including the alicyclic group);

R' represents an aliphatic diyl group having 5 to 60 carbon atoms, which is a group selected from the group consisting of an alicyclic group and an alkanediyl group having an alicyclic group at the terminal or in the chain thereof, when the aliphatic group has 5 to 8 carbon atoms;

a group selected from the group consisting of an alicyclic group, an alkanediyl group having an alicyclic group at the terminal or in the chain thereof, and an alkanediyl group having a branch, when the aliphatic group has 9 to 19 carbon atoms; or a group selected from the group consisting of an alicyclic group, an alkanediyl group having an alicyclic group at the terminal or in the chain thereof, an alkanediyl group having a branch, and a linear alkanediyl group, when the aliphatic group has 20 to 60 carbon atoms;

R and n have the same meaning as those described in the general formula (I).)

According to a second aspect, the present invention provides an ultraviolet absorber for synthetic resins according to the first aspect, in which in the above-mentioned general formula (I), X is a group represented by (a) or (d).

According to a third aspect, the present invention provides an ultraviolet absorber for synthetic resins according to the first or the second aspect, in which in the general formula (I), and in the group represented by X in the above-mentioned general formula (I), n is 0.

According to a fourth aspect, the present invention provides a synthetic resin composition comprising 100 parts by mass of a synthetic resin having compounded therein 0.001 to 25 parts by mass of the ultraviolet absorber for synthetic resins according to any one of the first to the third aspects.

According to a fifth aspect, the present invention provides a synthetic resin composition according to the fourth aspect, further containing 0.001 to 10 parts by mass of at least one hindered amine light stabilizer.

According to a sixth aspect, the present invention provides a synthetic resin composition according to the fourth or the fifth aspect, in which the synthetic resin is selected from polycarbonate resins, polyolefin resins and polyester resins.

BEST MODE FOR CARRYING OUT THE INVENTION

Hereinafter, embodiments of the present invention will be described.

The ultraviolet absorber for synthetic resins according to the present invention is composed of a triazine compound having a structure represented by the general formula (1) shown above.

In the groups (a) to (d) represented by X in the general formula (I) shown above, $R^1$, $R^{40}$ and $R^2$ contribute to giving the ultraviolet absorber compatibility and/or dispersibility with synthetic resins, with a greater number of carbon atoms thereof giving better compatibility and/or dispersibility. If the compatibility and/or dispersibility is good, the ultraviolet stabilizing effect becomes better even when the same amount of the ultraviolet absorbing groups is added. In contrast, if the number of carbon atoms becomes larger, the proportion of the triazine skeleton having the ability of absorbing ultraviolet rays becomes smaller, so that no sufficient effect of addition can be obtained.

Concerning $R^1$ and R', these may have a small number of carbon atoms since alkyl groups or alkanediyl groups having an alicyclic group or a branch have better compatibility and/or dispersibility as compared with linear alkyl groups or alkanediyl groups. The alkyl group or alkanediyl group having an alicyclic group has 5 to 60 carbons. The alkyl group or alkanediyl group having a branch has 9 to 60 carbon atoms. The linear alkyl group or alkanediyl group has 20 to 60 carbon atoms.

Also, $R^2$ has 1 to 18 carbon atoms.

The triazine compound in accordance with the present invention in which X is (a) will be illustrated.

In the case where $R^1$ is an alicyclic group or has an alicyclic group at the terminal or in the chain thereof, it has 5 to 60 carbon atoms, preferably 5 to 19 carbon atoms. The triazine compound having an alicyclic group has good heat resistance and hence has the feature that it has good initial coloring due to processing temperature when it is compounded with synthetic resins.

The above-mentioned alicyclic group or $R^1$ having an alicyclic group at the terminal or in the chain thereof preferably includes, for example, groups represented by the following general formula (1) or (2). Note that in the present invention, the alicyclic group is a concept that includes those having one or two unsaturated bonds in the ring structure.

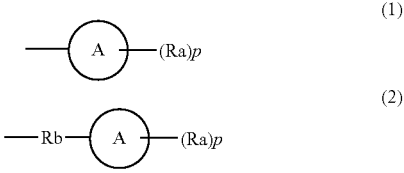

(wherein the ring A represents an alicyclic group having 5 to 8 carbon atoms that may have one or two unsaturated bonds in the ring structure, Ra represents an alkyl group, Rb represents an alkanediyl group, and p is 0 or an integer of up to 4, provided that the sum of the carbon atoms in the group is from 5 to 19.)

In the above-mentioned general formulas (1) and (2), specific examples of the ring A include a cyclopentane ring, a cyclohexane ring, a cyclooctane ring, a bicycloheptane ring, a bicyclohexane ring, a bicyclooctane ring, and a compound which has one or two unsaturated bonds in a ring structure thereof. Specific examples of the alkyl group Ra include methyl, ethyl, propyl, isopropyl, butyl, secondary butyl, tertiary butyl, pentyl, hexyl, and octyl. Specific examples of the alkanediyl Rb include methylene, ethylene, propylene, butylene, pentylene, hexylene, octylene, and decylene.

In $R^1$ which has the above-mentioned alicyclic group or which has the alicyclic group at the terminal or in the chain thereof, examples of $R^1$ which has the alicyclic group at the terminal thereof include cyclopentyl, 2-cyclopentylethyl, 3-cyclopentylpropyl, 4-cyclopentylbutyl, 5-cyclopentylpentyl; cyclohexyl, 1-methylcyclohexyl, cyclohexylmethyl, 2-cyclohexylethyl, 3-cyclohexylpropyl, 4-cyclohexylbutyl, 5-cyclohexylpentyl, 8-cyclohexyloctyl, 10-cyclohexyldecyl; cycloheptyl; cyclooctyl; bicyclohexyl, bicycloheptyl, and bicyclooctyl.

Examples of those which has the alicyclic group in the chain thereof include 2-methylcyclohexyl; 3-methylcyclohexyl; 4-methylcyclohexyl; 2,4-dimethylcyclohexyl; 2,5-dimethylcyclohexyl; 2,6-dimethylcyclohexyl; 3,4-dimethylcyclohexyl; 4,5-dimethylcyclohexyl; 4-ethylcyclohexyl; 4-propylcyclohexyl; 4-isopropylcyclohexyl; 4-butylcyclohexyl; 4-tert-butylcyclohexyl; 4-hexylcyclooctyl; 4-cyclohexyldecyl; (4-methylcyclohexyl)methyl; 2-(4-ethylcyclohexyl)ethyl; and 3-(4-isopropylcyclohexyl)propyl.

Further specific examples of $R^1$ of the triazine compound used in the present invention that is an alicyclic group or that has an alicyclic group at the terminal or in the chain thereof include Compounds Nos. 1 to 6 shown below.

Compound No. 1

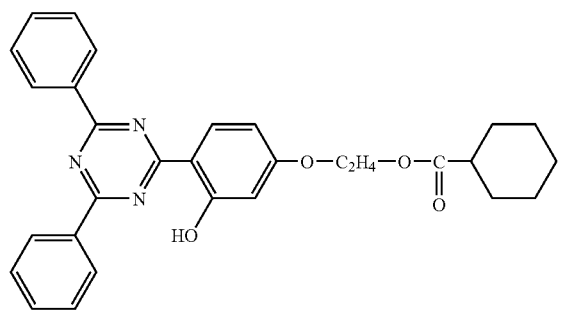

Compound No. 2

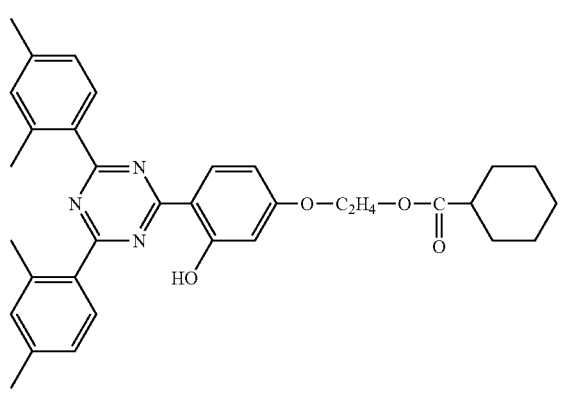

Compound No. 3

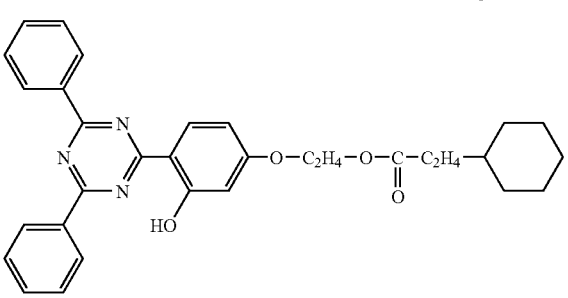

Compound No. 4

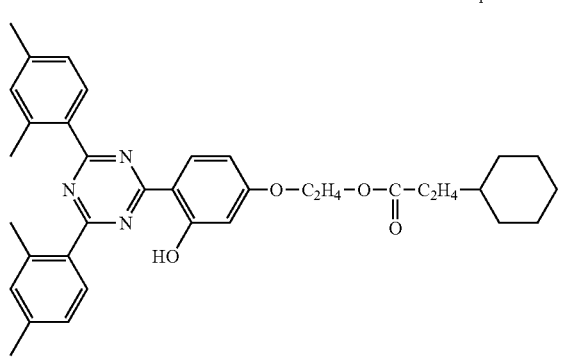

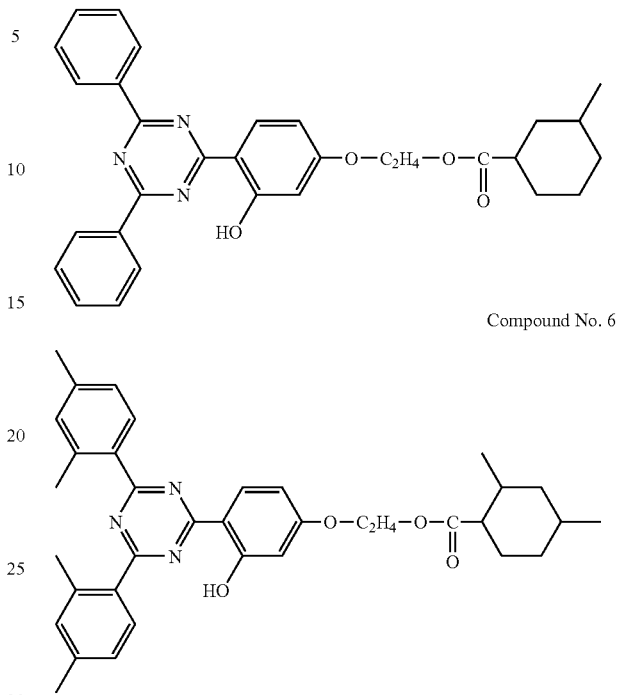

When it is an alkyl group having a branch, $R^1$ of the triazine compound in accordance with the present invention has 9 to 60 carbon atoms.

In this case, $R^1$ is a group derived from the corresponding aliphatic carboxylic acid. Examples of the aliphatic carboxylic acid which derives the group include 2-(3-methylbutyl)-7-methyloctanoic acid; 2-(1-methylbutyl)-5-methyloctanoic acid; 2-hexyldecanoic acid; 2-heptyldecanoic acid; 2-(1,3,3-trimethylbutyl)-5,7,7-trimethyloctanoic acid; 2-(3-methylhexyl)-7-methyldecanoic acid; 2-octyldodecanoic acid; 2-methylicosanoic acid; 2-propyloctadecanoic acid; 2-butyloctadecanoic acid; 2-methyldocosanoic acid; 10-methyldocosanoic acid; 2-pentyloctadecanoic acid; 2-methyltricosanoic acid; 3-methyltricosanoic acid; 22-methyltricosanoic acid; 20-ethyldocosanoic acid; 18-propylhexaicosanoic acid; 2-hexyloctadecanoic acid; 12-hexyloctadecanoic acid; 2-methyltetracosanoic acid; 3-methyltetracosanoic acid; 6-methyltetracosanoic acid; 10-methyltetracosanoic acid; 12-methyltetracosanoic acid; 14-methyltetracosanoic acid; 18-methyltetracosanoic acid; 23-methyltetracosanoic acid; 9-heptyloctadecanoic acid; 9-octylheptadecanoic acid; 24-methylheptacosanoic acid; 2-ethyltetracosanoic acid; 2-butyldocosanoic acid, 2-hexylicosanoic acid; 2-octyloctadecanoic acid; 2-undecylpentadecanoic acid; 2-decylhexadecanoic acid; 2-methylhexacosanoic acid; 10-methylhexacosanoic acid; 2-nonyloctandecanoic acid; 2-decyloctadecanoic acid; 2-hendecyloctadecanoic acid; 2-dodecyloctadecanoic acid; 33-methyltetratriacontanoic acid; 20,20-dimethylhenicosanoic acid; 13,16-dimethyltricosanoic acid; 14,17-dimethyltetracosanoic acid; 3,13,19-trimethyltricosanoic acid; and 3,13-dimethylpentacosanoic acid.

The alkyl group having a branch, represented by $R^1$ described above, preferably has 9 to 19 carbon atoms in consideration of good compatibility and/or dispersibility with synthetic resins and proportion of a benzotriazole skeleton having an ultraviolet absorbability. A 1-alkylalkane-1-yl group having 9 to 19 carbon atoms represented by the following general formula (3) is more preferred.

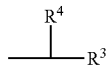
(3)

(Wherein $R^3$ is an alkyl group having 4 to 17 carbon atoms which may be branched, $R^4$ is an alkyl group having 1 to 9 carbon atoms which may be branched, provided that the number of carbon atoms in $R^3$ is identical to or greater than that in $R^4$.)

In the case where the triazine compound having an alkyl group having a branch in $R^1$ as described above is used for polyolefin resins, those having 14 to 19 carbon atoms are preferable since they give rise to synthetic resin compositions having low turbidity and good transmittance. The side chain ($R^4$ in the above-mentioned general formula (3)) is preferably one having 3 or more carbon atoms, more preferably 5 or more carbon atoms.

The above-mentioned preferred $R^1$ group is a group derived from the aliphatic carboxylic acid having a branch at the alpha position. Examples of the aliphatic carboxylic acid with a branch at the alpha position include 2-(3-methylbutyl)-7-methyloctanoic acid; 2-(1-methylbutyl)-5-methyloctanoic acid; 2-hexyldecanoic acid; 2-heptyldecanoic acid; 2-(1,3,3-trimethylbutyl)-5,7,7-trimethyloctanoic acid; 2-(3-methylhexyl)-7-methyldecanoic acid; and 2-octyldodecanoic acid.

Further specific examples of the triazine compound in accordance with the present invention in which the above-mentioned $R^1$ is the alkyl group having a branch as a preferred form include the following Compounds Nos. 7 to 11.

Compound No. 7

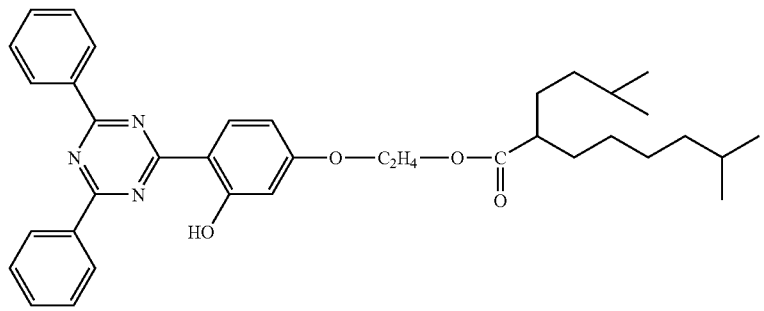

Compound No. 8

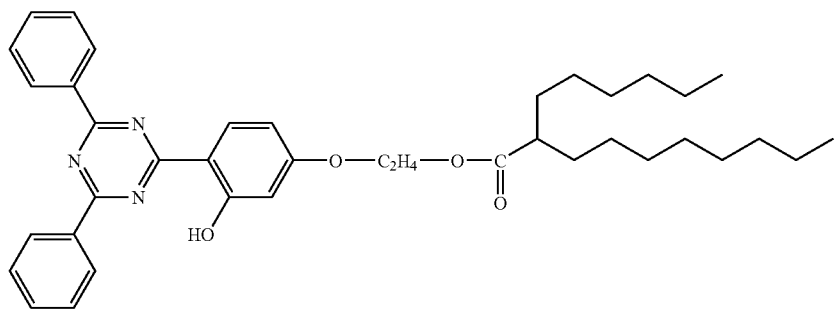

Compound No. 9

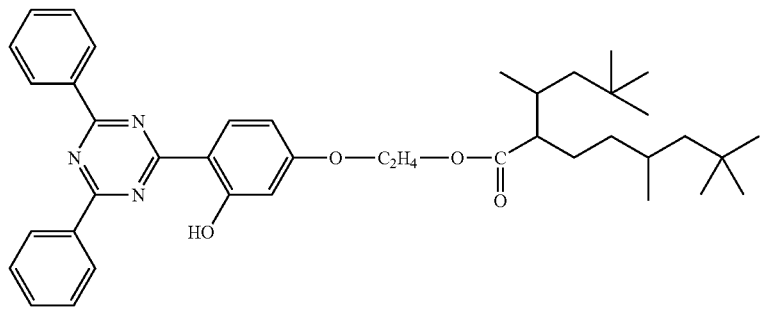

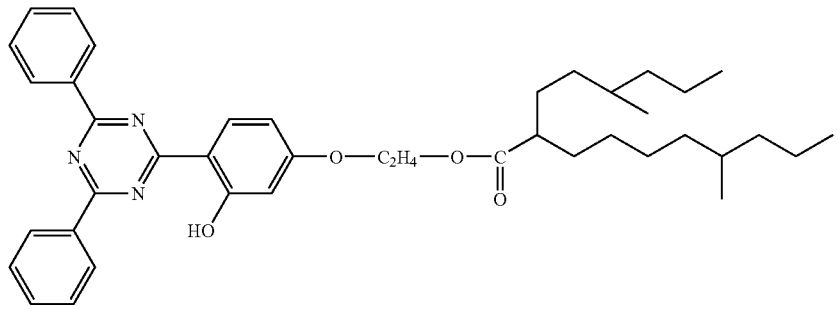

Compound No. 10

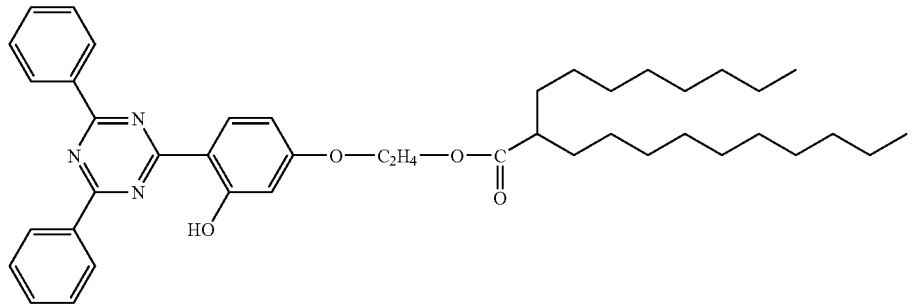

Compound No. 11

When it is a linear alkyl group, $R^1$ of the triazine compound used in accordance with the present invention has 20 to 60 carbon atoms.

In this case, $R^1$ is a group derived from the corresponding linear aliphatic carboxylic acid. Examples of the aliphatic carboxylic acid which derives the group include linear carboxylic acids such as henicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, pentatriacontanoic acid, hexatriacontanoic acid, heptatriacontanoic acid, octatriacontanoic acid, tetracontanoic acid, hexatetracontanoic acid, pentacontanoic acid, and hexacontanoic acid.

The linear alkyl group is preferably one that has 20 to 30 carbon atoms that have good compatibility and/or dispersibility with synthetic resins and suitable proportions of the benzotriazole skeleton having ultraviolet absorbability.

Specific examples of the preferred benzotriazole compound described above include, for example, the following Compounds Nos. 12 to 16.

Compound No. 12

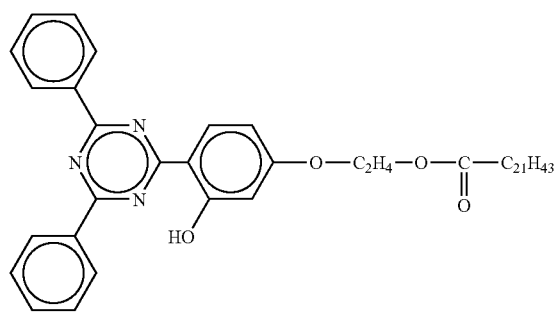

Compound No. 13

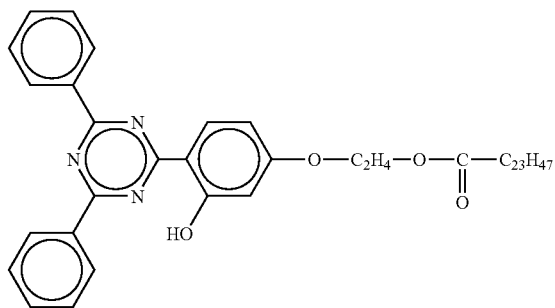

Compound No. 14

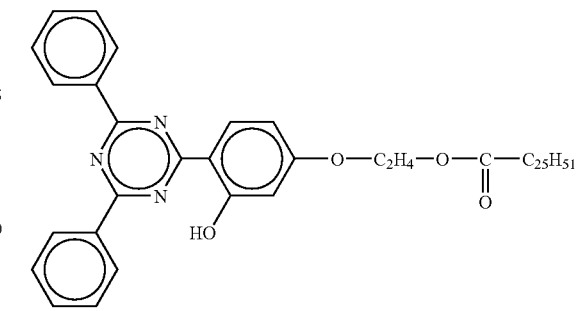

-continued

Compound No. 15

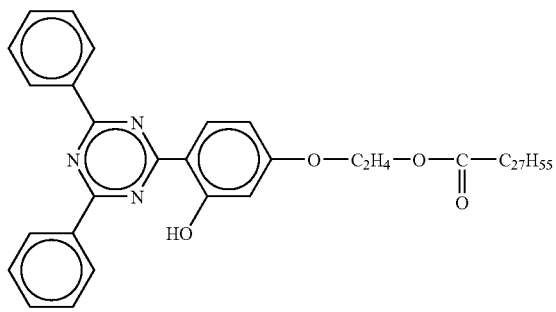

Compound No. 16

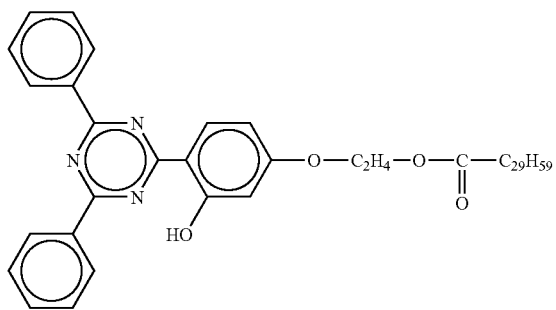

Next, the triazine compounds in accordance with the present invention in which X is (b) or (c) will be illustrated.

In this case, R' is an alicyclic group or an alkanediyl having an alicyclic group at the terminal or in the chain thereof, having 5 to 60 carbon atoms, an alkanediyl having a branch, having 9 to 60 carbon atoms, or a linear alkanediyl having 20 to 60 carbon atoms. Preferred among these is an alicyclic group or an alkanediyl having an alicyclic group at the terminal or in the chain thereof, more preferably it is one that has 5 to 19 carbon atoms.

The alkanediyl group having an alicyclic group in the chain thereof or an alicyclic group having 5 to 19 carbon atoms represented by R', which is a preferred form of the triazine compound in which X is (b) or (c), includes, for example, the group represented by the following general formula (4).

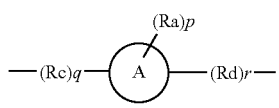

(4)

(Wherein the ring A, Ra and p are the same as those described in the general formula (1) shown above, Rc and Rd each represent an alkanediyl group, and q and r are each 0 or 1, provided that the sum of carbon atoms of the entire group is 5 to 19.)

R' described above is derived from an organic dicarboxylic acid or an acid anhydride which has an alicyclic group. The organic dicarboxylic acid includes 1,2-cyclopentanedicarboxylic acid; 1,3-cyclopentanedicarboxylic acid; 1,2-cyclohexanedicarboxylic acid; 1,3-cyclohexanedicarboxylic acid; 1,4-cyclohexanedicarboxylic acid; and 1,4-dicarboxylmethylenecyclohexane. The acid anhydride includes methyltetrahydrophthalic anhydride, tetrahydrophthalic anhydride, nadic anhydride, methyl nadic anhydride, trialkyltetrahydrophthalic anhydride, hexahydrophthalic anhydride, and methylhexahydrophthalic anhydride.

Specific examples of the triazine compound in which X is (b) include the following Compounds, No. 17 to 22.

Compound No. 17

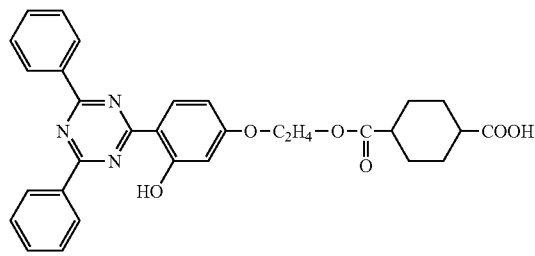

Compound No. 18

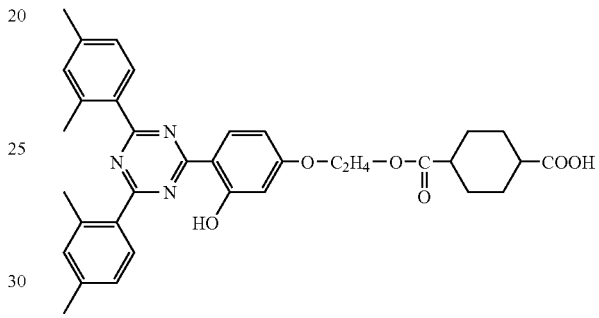

Compound No. 19

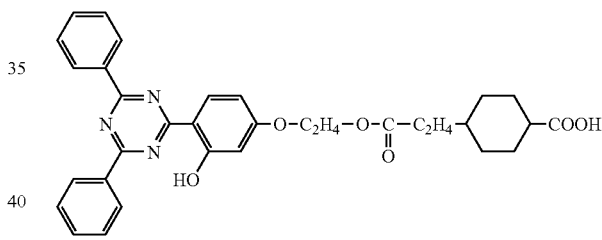

Compound No. 20

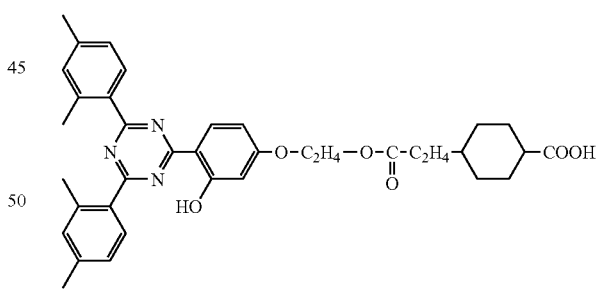

Compound No. 21

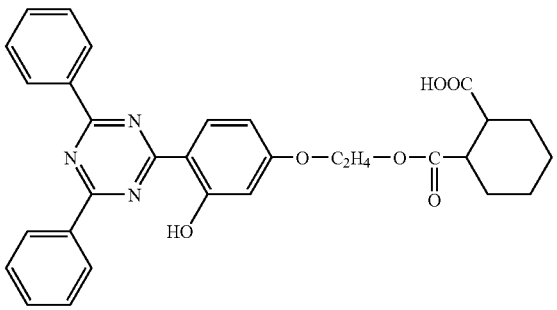

-continued

Compound No. 22

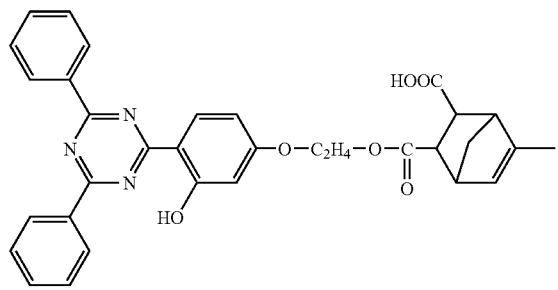

Also, in the case where in the above-mentioned general formula (I), X is represented by C, R² is a group selected from the group consisting of an alkyl group having 1 to 18 carbon atoms, which may be branched or may have an alicyclic group at the terminal or in the chain thereof, and a (poly)alkyleneoxyalkyl group (with the number of carbon atoms including the alicyclic group);

The alkyl group having 1 to 18 carbon atoms which may be branched or have an alicyclic group at the terminal or in the chain thereof include methyl, ethyl, propyl, isopropyl, butyl, secondary butyl, tertiarybutyl, isobutyl, amyl, isoamyl, tertiaryamyl, cyclopentyl, hexyl, cyclohexyl, heptyl, 2-heptyl, 3-heptyl, isoheptyl, tertiary heptyl, n-octyl, isooctyl, tertiary octyl, 2-ethylhexyl, nonyl, isononyl, decyl, dodecyl, tridecyl, tetradecyl, pentadecyl, hexadecyl, heptadecyl, and octadecyl.

The (poly)alkyleneoxyalkyl group having 1 to 18 carbon atoms include methoxyethyl, ethoxymethyl, propoxyethyl, butoxyethyl, 2-(2-methoxyethoxy)ethyl, 2-(2-butoxyethoxy)ethyl, and 2-[2-(2-methoxyethoxy)ethoxy]ethyl.

Specific examples of the triazine compound in which X is (c) include compounds Nos. 23 to 28.

Compound No. 23

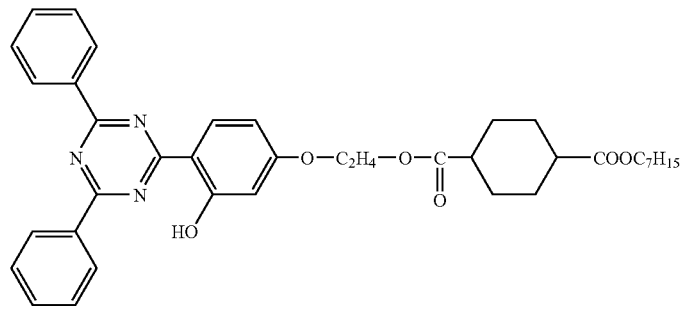

Compound No. 24

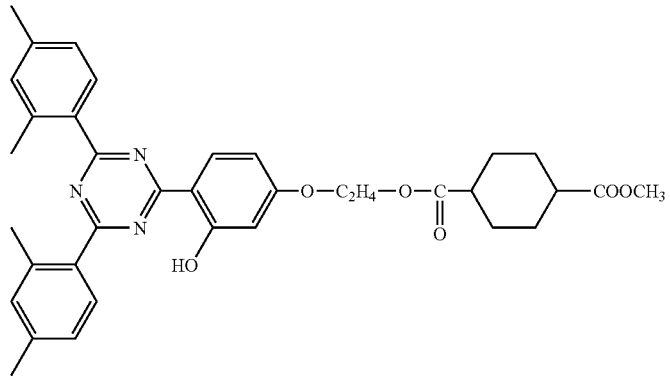

Compound No. 25

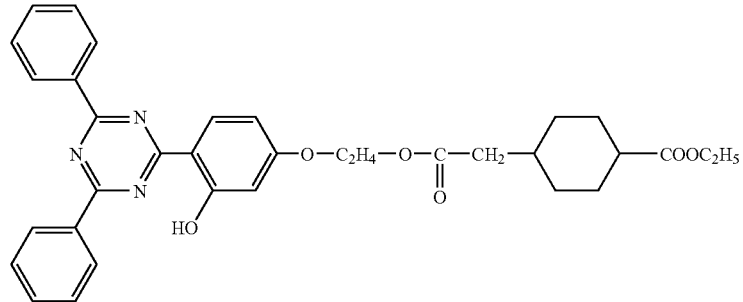

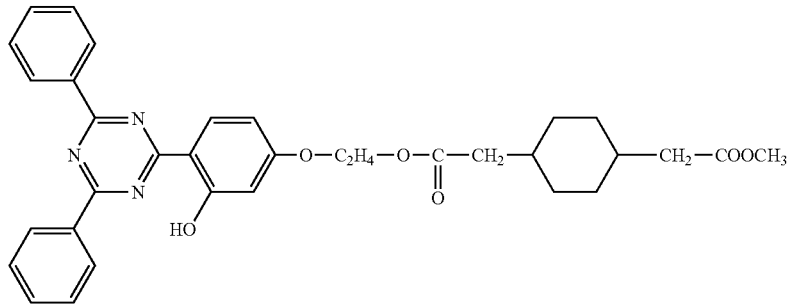

Compound No. 26

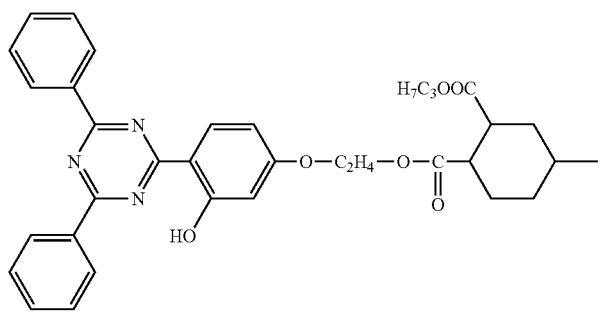

Compound No. 27

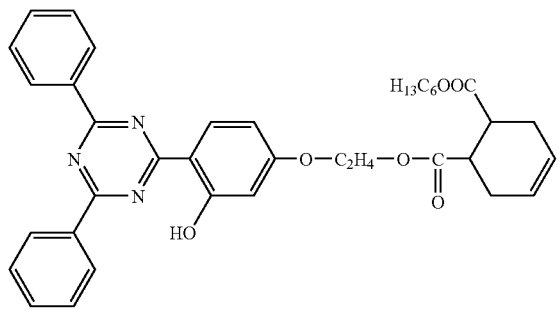

Compound No. 28

Next, the triazine compounds in accordance with the present invention in which X is (d) will be illustrated.

In this case, R' is an alicyclic group or an alkanediyl having an alicyclic group at the terminal or in the chain thereof, having 5 to 60 carbon atoms, an alkanediyl having a branch, having 9 to 60 carbon atoms, or a linear alkanediyl having 20 to 60 carbon atoms.

The alkanediyl group represented by R' is derived from the corresponding organic dicarboxylic acid or the dicarboxylic anhydride. The organic dicarboxylic acid or the dicarboxylic anhydride having 5 to 60 carbon atoms which introduces an alicyclic group or an alkanediyl with an alicyclic group at the terminal or in the chain include 1,2-cyclopentanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid, 1,4-dicarboxylmethylenecyclohexane, dimer acid, and hydrogenated dimer acid. The acid anhydride includes methyltetrahydrophthalic anhydride, tetrahydrophthalic anhydride, nadic anhydride, methyl nadic anhydride, trialkyltetrahydrophthalic anhydride, hexahydrophthalic anhydride, and methylhexahydrophthalic anhydride.

The organic dicarboxylic acid or the dicarboxylic anhydride which introduces an alkanediyl group having a branch includes 8,13-dimethyl-1-,18-octadecamethylenedicarboxylic acid. The organic dicarboxylic acid or the dicarboxylic anhydride which introduces a linear alkanediyl group include 1-,20-icosamethylenedicarboxylic acid, 1-20-henicosamethylenedicarboxylic acid, 1-,22-docosamethylenedicarboxylic acid, 1-,24-tetracosamethylenedicarboxylic acid, 1-,28-octacosamethylenedicarboxylic acid, and 1-,32-dotriacontanemethylenedicarboxylic acid.

R' in the groups represented by (d) are preferably alicyclic groups having 5 to 60 carbon atoms or alkanediyls having an alicyclic group at the terminal or in the chain thereof. Specific examples of triazine compounds having such preferred (R')s include Compounds Nos. 29 to 43 shown below.

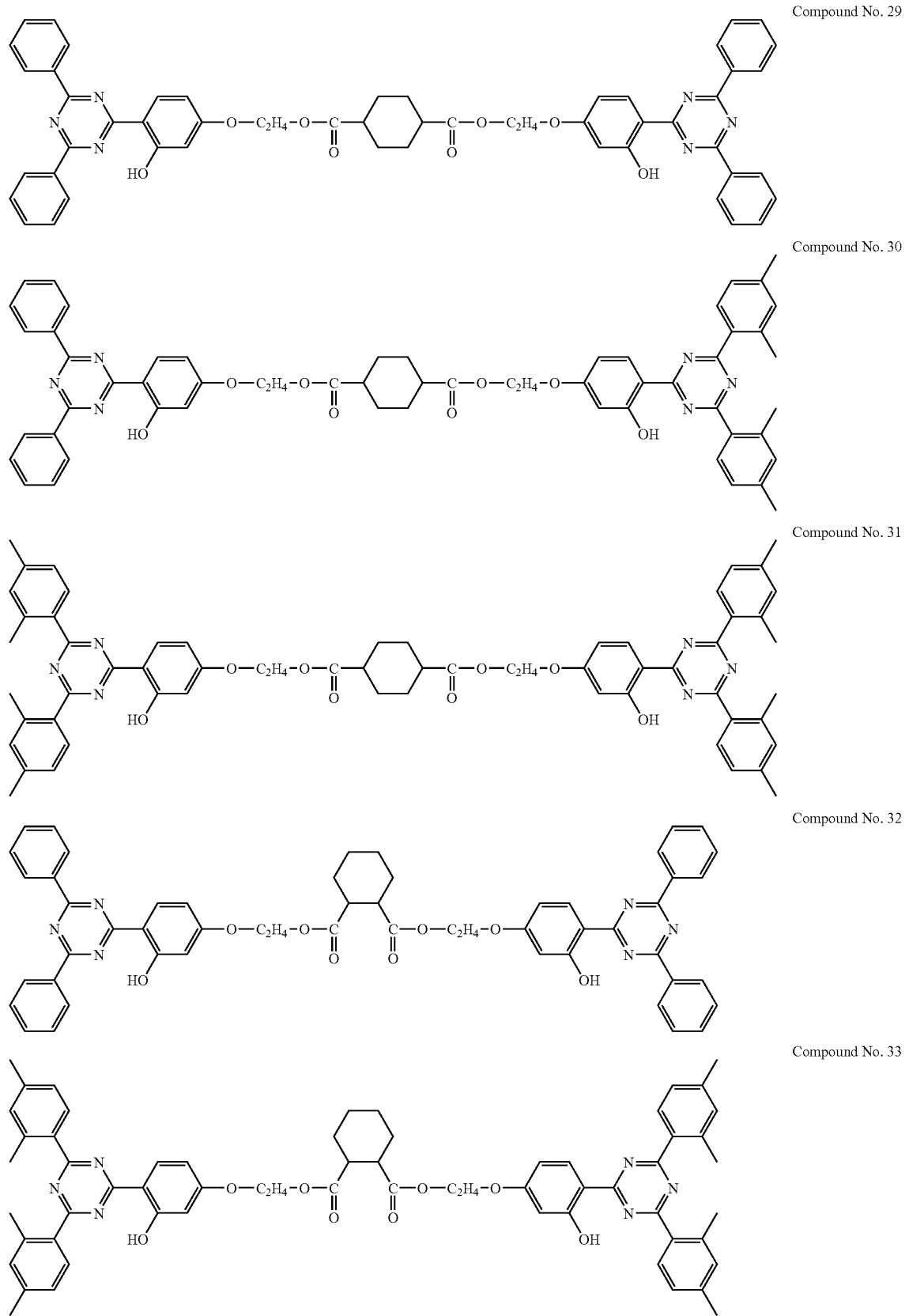

-continued
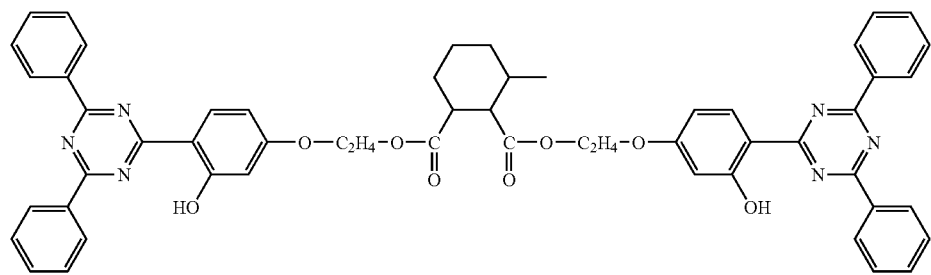
Compound No. 34
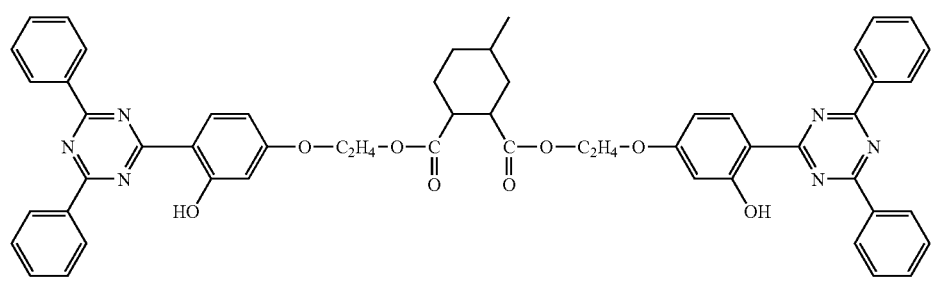
Compound No. 35
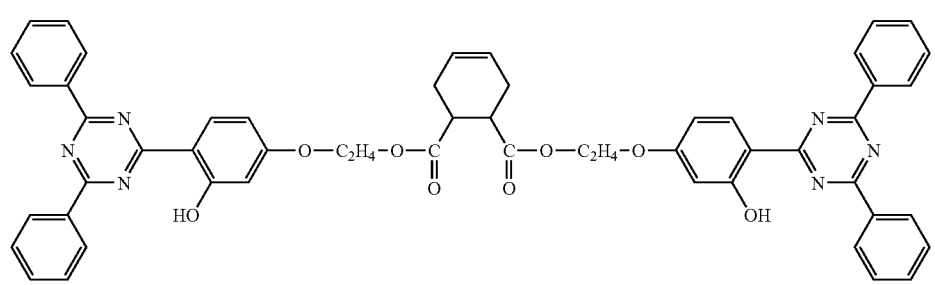
Compound No. 36
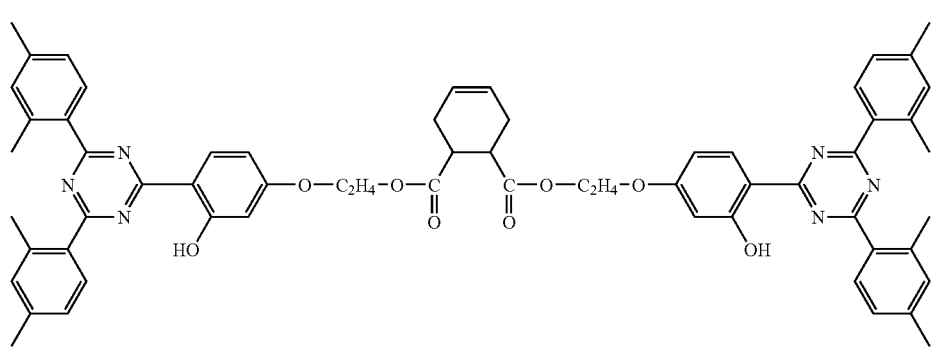
Compound No. 37
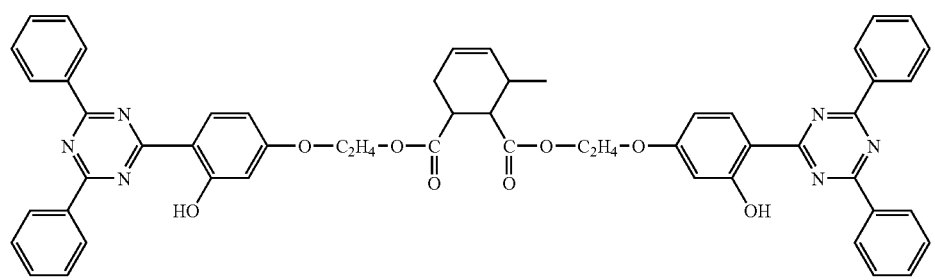
Compound No. 38

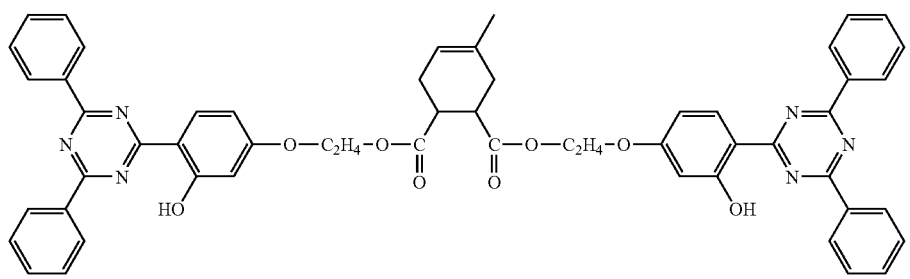

Compound No. 39

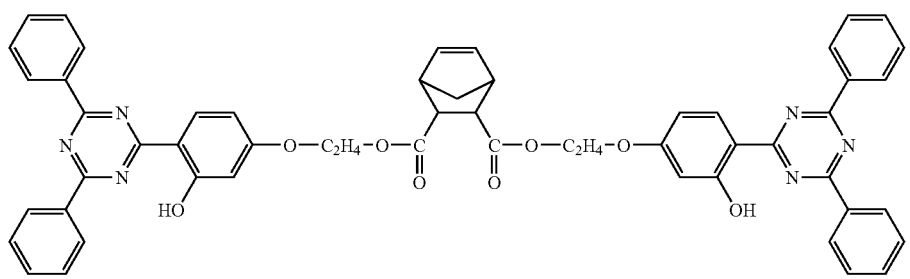

Compound No. 40

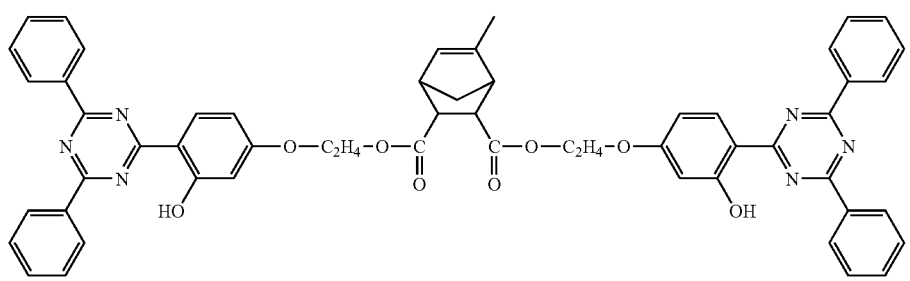

Compound No. 41

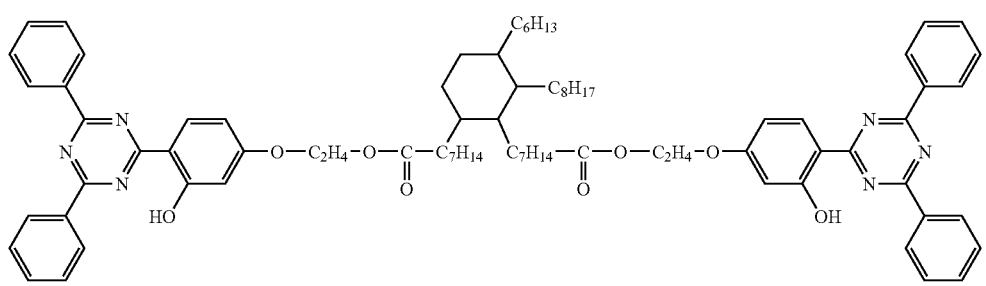

Compound No. 42

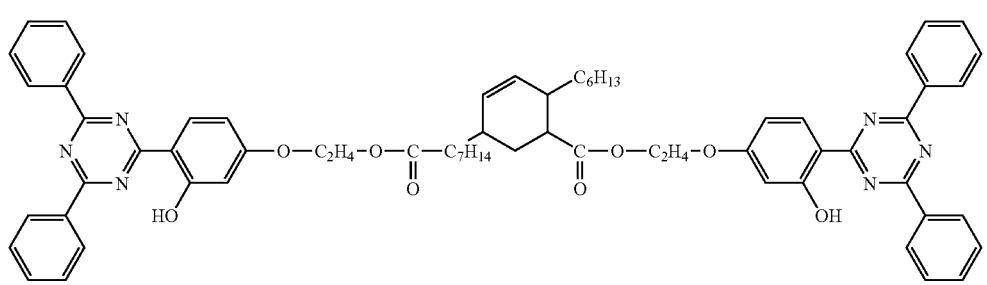

Compound No. 43

In the general formula (I) shown above according to the present invention, the alkyl groups having 1 to 4 carbon atoms represented by R include methyl, ethyl, propyl, isopropyl, butyl, secondary butyl, tertiary butyl, isobutyl, etc.

Those represented by the general formula (I) shown above in which n is 0 are preferred since they cause least coloring of the synthetic resin composition.

The method of producing the triazine compounds represented by the general formula (I) above according to the present invention is not particularly limited and general well-known methods may be used.

In the case where X is a group represented by (a), the triazine compound can be obtained by esterification reaction or interesterification reaction between, for example, a 2-[2- hydroxy-4-(2-hydroxyethyloxy)phenyl]-4,6-diphenyl-1,3,5-triazine derivative and an ester deriving compound of the corresponding a liphatic carboxylic acid (aliphatic carboxylic acid, aliphatic carboxyl halide or aliphatic carboxylic acid ester).

In the case where X is a group represented by (b), the triazine compound can be obtained by esterification reaction or interesterification reaction between, for example, a 2-[2-hydroxy-4-(2-hydroxyethyloxy)phenyl]-4,6-diphenyl-1,3,5-triazine derivative and an ester deriving compound of a corresponding organic dicarboxylic acid (organic dicarboxylic acid, organic dicarboxylic acid monohalide or monoester of organic dicarboxylic acid).

In the case of the group where X is represented by (c), it is obtained by, for example, esterification reaction between a corresponding alcohol compound and a compound in which X is represented by b, esterification reaction or interesterification reaction between 2-[2-hydroxy-4-(2-hydroxyethyloxy)phenyl]-4,6-diphenyl-1,3,5-triazine derivative and a corresponding ester deriving compound (organic dicarboxylic acid monoester, organic dicarboxylic acid monoester monohalide or organic dicarboxylic acid diester), or the esterification reaction or interesterification reaction between an alcohol component (between a corresponding alcohol and 2-[2-hydroxy-4-(hydroxyethyloxy)phenyl]-4,6-diphenyl-1,3,5-triazine derivative), and an organic dicarboxylic acid ester deriving compound (organic dicarboxylic acid, organic dicarboxylic acid dihalide, organic dicarboxylic acid diester, acid anhydride).

In the case of the group where X is represented by (d), it is obtained by, for example, esterification reaction or interesterification reaction between 2-[2-hydroxy-4-(2-hydroxyethyloxy)phenyl]-4,6-diphenyl-1,3,5-triazine derivative and ester deriving compound of the corresponding organic diacarboxylic acid (organic dicarboxylic acid, organic dicarboxylic acid dihalide, organic dicarboxylic acid diester, acid anhydride).

The synthetic resin used in the present invention for the synthetic resin composition containing an ultraviolet absorber composed of a triazine compound represented by the above-mentioned general formula (I) include α-olefin polymers such as a low-density polyethylene, a linear low-density polyethylene, a high-density polyethylene, a polypropylene, a polybutane-1, a poly(3-methylbutene), and a poly(4-methylpentene) or an ethylene-vinyl acetate copolymers; polyolefin resins such as an ethylene/propylene block or random copolymer, and copolymers thereof; halogen-containing resins such as a polyvinyl chloride, a polyvinylidene chloride, a chlorinated polyethylene, a polyvinylidene fluoride, a chlorinated rubber, a vinyl chloride-vinyl acetate copolymer, a vinyl chloride-ethylene copolymer, a vinyl chloride-vinylidene chloride-vinyl acetate terpolymer, a vinyl chloride-acrylate ester copolymer, a vinyl chloride-maleic acid ester copolymer, and a vinyl chloride-cyclohexylmaleimide copolymer; polyester resins such as a polyethylene terephthalate (PET), a polybutylene terephthalate (PBT), and a polyhexamethylene terephthalate; styrene resins such as apolystyrene, a high-impact polystyrene (HIPS), an acrylonitrile butadiene styrene (ABS), a chloride polyethylene acrylonitrile styrene (ACS), a styrene acrylonitrile (SAN), acrylonitrile butyl acrylate styrene (AAS), butadiene styrene, styrene maleic acid, styrenemaleimide, anacrylonitrile ethylenepropylene styrene (AES), and a methyl methacrylate butadiene styrene (MBS); polycarbonate resins such as a polycarbonate and a branched polycarbonate; polyamide resins such as a polyamide using an aromatic dicarboxylic acid including a polyhexamethyleneadipamide (nylon 66), a polycaprolactam (nylon 6), and a nylon 6T, or a alicyclic dicarboxylic acid; a polyphenyleneoxide (PPO) resin, a modified polyphenyleneoxide resin, a polyphenylenesulfide (PPS) resin, a polyacetal (POM), a modified polyacetal, a petroleum resin, a coumarone resin, a polyvinyl acetate resin, an acrylic resin, a polymer alloy between a polycarbonate and a styrene resin, LCP; silicon resins; urethane resins; aliphatic dicarboxylic acids, aliphatic diols, aliphatic hydroxy carboxylic acids or an aliphatic polyester derived from its ring compound, and further biodegradable resins such as an aliphatic polyester in which the molecular weight has increased due to diisocyanate; cellulose resins; and recycled resins thereof.

In the synthetic resin composition of the present invention, the compounding amount of the ultraviolet absorber composed of a triazine compound is not particularly limited and any value may be selected. It is preferably 0.001 to 25 parts by mass, more preferably 0.01 to 15 parts by mass since less than 0.001 part by mass per 100 parts by mass of synthetic resin in some cases gives no effect while above 25 parts by mass results not only in a failure of giving an increased effect of addition but also increases the cost.

Furthermore, in the case where further stabilization is to be imparted, additives such as hindered amine light stabilizers, phenol, and sulfur or phosphorus antioxidants may be added to the synthetic resin composition of the present invention. Also, ultraviolet absorbers other than the compounds represented by the general formula (I) above according to the present invention may be used in combination.

In particular, hindered amine light stabilizers (hereinafter sometimes referred to as HALS) have the function of imparting resins and resin compositions with weatherability as a result of capturing decomposable radicals derived from resins generated due to ultraviolet rays, light or heat and oxide compounds in the resin composition by the nitrogen at the 1-position of N-proton, N-oxyl, N-oxyalkyl, N-alkyl, N-hydroxy or the like in the molecule and a functional group bonded thereto. Use of them in combination with ultraviolet absorbers can give rise to synergistic effects, so that they can be preferably used for particularly polyolefin resins.

The above-mentioned HALS includes compounds represented by the following general formula (II) cyanuric chloride-condensed type, high molecular weight type, etc.

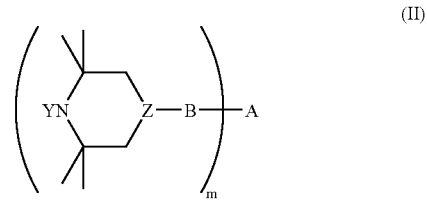

(II)

(Wherein m is an integer of 1 to 6, A represents a hydrogen atom, an m-valent hydrocarbon group having 1 to 18 carbon atoms, an m-valent acyl group, or an m-valent carbamoyl group, B represents an oxygen atom, —NH—, or —NRe— having an alkyl group Re having 1 to 8 carbon atoms, Y represents a hydrogen atom, an oxy radical (.O), an alkoxy group having 1 to 18 carbon atoms, an alkyl group having 1 to 8 carbon atoms, or a hydroxyl group, Z represents a methyne, or a group (III) having an alkyl group Rf having 1 to 8 carbon atoms.)

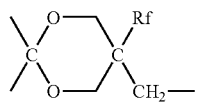 (III)

In the general formula (II) shown above, examples of the m-valent hydrocarbon group having 1 to 18 carbon atoms which is represented by A include groups (an alkyl group and an alkandiyl to an alkanhexayl group) derived from methane, ethane, propane, butane, secondary butane, tertiary butane, isobutane, pentane, isopentane, tertiary pentane, hexane, cyclohexane, heptane, isoheptane, tertiaryheptane, n-octane, isooctane, tertiaryoctane, 2-ethylhexane, nonane, isononane, decane, dodecane, tridecane, tetradecane, pentadecane, hexadecane, heptadecane, andoctadecane.

The m-valent acyl group in A described above means those groups derived from carboxylic acids, m-valent carboxylic acids, and (n-m) alkyl esters of n-valent carboxylic acids with m carboxyl groups remaining (these being referred to as acyl derivative compounds).

The acyl derivative compounds include acetic acid, benzoic acid, 4-trifluoromethylbenzoic acid, salicylic acid, acrylic acid, methacrylic acid, oxalic acid, malonic acid, succinic acid, glutaric acid, adipic acid, pimelic acid, suberic acid, azelaic acid, sebacic acid, dodecanoic diacid, 2-methylsuccinic acid, 2-methyladipic acid, 3-methyladipic acid, 3-methylpentanediacid, 2-methyloctanediacid, 3,8-dimethyldecane diacid, 3,7-dimethyldecane diacid, hydrogenated dimer acid, dimer acid, phthalic acid, terephthalic acid, isophthalic acid, naphthalenedicarboxylic acid, cyclohexanedicarboxylic acid, trimellitic acid, trimesic acid, propane-1,2,3-tricarboxylic acid, propane-1,2,3-tricarboxylic acid monoalkyl or dialkyl ester, pentane-1,3,5-tricarboxylic acid, pentane-1,3,5-tricarboxylic acid monoalkyl or dialkyl ester, butane-1,2,3,4-tetracarboxylic acid, butane-1,2,3,4-tetracarboxylic acid monoalkyl to trialkyl ester, pentane-1,2,3,4,5-pentacarboxylic acid, pentane-1,2,3,4,5-pentacarboxylic acid monoalkyl to tetraalkyl ester, hexane-1,2,3,4,5,6-hexacarboxylic acid, hexane-1,2,3,4,5,6-hexacarboxylic acid monoalkyl to pentaalkyl ester.

The m-valent carbamoyl group shown above as A means a monoalkylcarbamoyl group or a dialkylcarbamoyl group derived from isocyantate compounds.

The isocyanate compounds from which a monoalkylcarbamoyl group is derived include: tolylene diisocyanate; diphenylmethane-4,4'-diisocyanate; p-phenylene diisocyanate; xylylene diisocyanate; 1,5-naphthylene diisocyanate; 3,3'-dimethyldiphenyl-4,4'-diisocyanate; dianisidine diisocyanate; tetramethylxylylene diisocynate; isophorone diisocyanate; dicyclohexylmethane-4,4'-diisocyanate; trans-1,4-cyclohexyl diisocyanate; norbornene diisocyanate; 1,6-hexamethylene diisocyanate; 2,2,4(2,2,4)-trimethylhexamethylene diisocyanate; lysine diisocyanate; triphenylmethane triisocyanate; 1-methylbenzol-2,4,6-triisocyanate; and dimethyltriphenylmethane tetraisocyanate. The dialkylcarbamoyl group includes a diethylcarbamoyl group, a dibutylcarbamoyl group, a dihexylcarbamoyl group, and a dioctylcarbamoyl group.

These groups that are represented by A may be substituted by a halogen atom, a hydroxyl group, an alkyl group, an alkoxy group, a nitro group, a cyano group, or the like.

The alkyl group having 1 to 8 carbon atoms that is represented as Re and that is substituted by N in B of the formula (II) includes methyl, ethyl, propyl, isopropyl, butyl, secondary butyl, tertiary butyl, isobutyl, amyl, isoamyl, tertiary amyl, hexyl, cyclohexyl, heptyl, isoheptyl, tertiary heptyl, 1-ethylpentyl, n-octyl, isooctyl, tertiary octyl, and 2-ethylhexyl.

Y in the formula (II) represents a hydrogen atom, an oxyradical (.O), an alkoxy group having 1 to 18 carbon atoms, an alkyl group having 1 to 8 carbon atoms, or a hydroxyl group.

The above-mentioned alkoxy group having 1 to 18 carbon atoms includes methoxy, ethoxy, propoxy, isopropoxy, butoxy, secondary butyloxy, tertiary butyloxy, isobutyloxy, amyloxy, isoamyloxy, hexyloxy, heptyloxy, octyloxy, 2-ethylhexyloxy, nonyloxy, isononyloxy, decyloxy, dodecyloxy, tridecyloxy, tetradecyloxy, pentadecyloxy, hexadecyloxy, heptadecyloxy, andoctadecyloxy. Also, the alkyl group having 1 to 8 carbon atoms include the same groups given as the examples for Re.

The alkyl group having 1 to 8 carbon atoms represented as Rf in Z of the formula (II) includes the same groups given as examples for Re.

More specific examples of HALS represented in the above-mentioned general formula (II) include, for example:
2,2,6,6-tetramethyl-4-piperidyl stearate;
1,2,2,6,6-pentamethyl-4-piperidyl stearate;
2,2,6,6-tetramethyl-4-piperidyl benzoate;
bis(2,2,6,6-tetramethyl-4-piperidyl)sebacate;
bis(1,2,2,6,6-pentamethyl-4-piperidyl)sebacate;
bis(1-octoxy-2,2,6,6-tetramethyl-4-piperidyl)sebacate;
1,2,2,6,6,-pentamethyl-4-piperidyl methacrylate;
2,2,6,6-tetramethyl-piperidyl methacrylate;
tetrakis(2,2,6,6-tetramethyl-4-piperidyl)-1,2,3,4-butanetetrac arboxylate;
tetrakis(1,2,2,6,6-pentamethyl-4-piperidyl)-1,2,3,4,-butanetet racarboxylate;
bis(2,2,6,6-tetramethyl-4-piperidyl).bis(tridecyl)-1,2,3,4-butanetetracarboxylate;
bis(1,2,2,6,6-pentamethyl-4-piperidyl).bis(tridecyl)-1,2,3,4-butanetetracarboxylate;
bis(1,2,2,6,6-pentamethyl-4-piperidyl)-2-butyl-2-(3,5-ditertbutyl-4-hydroxybenzyl)malonate;
3,9-bis[1,1-dimethyl-2-{tris(2,2,6,6-tetramethyl-4-piperidyloxycarbonyloxy)butylcarbonyloxy}ethyl]-2,4,8,10-tetraoxaspiro[5, 5]undecane;
3,9-bis[1,1-dimethyl-2-{(tris(1,2,2,6,6-pentamethyl-4-piperidyloxycarbonyloxy)butylcarbonyloxy}ethyl]-2,4,8,10-tetraoxaspiro[5,5]undecane, and the like.

The cyanuric chloride-condensed type HALS includes:
1,6-bis(2,2,6,6-tetramethyl-4-piperidylamino)hexane/2,4-dichloro-6-morpholino-s-triazine polycondensate;
1,6-bis(2,2,6,6-tetramethyl-4-pipieridylamino)hexane/2,4-dichloro-6-tert-octylamino-s-triazine polycondensate;
1,5,8,12-tetrakis[2,4-bis(N-butyl-N-(2,2,6,6-tetramethyl-4-piperidyl)amino)-s-triazine-6-yl]-1,5,8,12-tetraazadodecane;
1,5,8,12-tetrakis[2,4-bis(N-butyl-N-(1,2,2,6,6-pentamethyl-4-piperidyl)amino)-s-triazine-6-yl]-1,5,8,12-tetraazadodecane;
1,6,11-tris[2,4-bis(N-butyl-N-(2,2,6,6-tetramethyl-4-piperidyl)amino)-s-triazine-6-ylamino]undecane; and
1,6,11-tris[2,4-bis(N-butyl-N-(1,2,2,6,6-pentamethyl-4-piperidyl)amino)-s-triazine-6-ylamino]undecane, and the like.

Also, the high molecular weight types include 1-(2-hydroxyethyl)-2,2,6,6-tetramethyl-4-piperidinol/diethylsuccinate polycondensate,
1,6-bis(2,2,6,6-tetramethyl-4-piperidylamino)hexane/dibromoethane polycondensate, and the like, and the like.

The above-mentioned HALS may be used singly or as mixtures of two or more of them. The total compounding amount of the HALS is preferably 0.001 to 10 parts by mass, more preferably 0.01 to 2 parts by mass, per 100 parts by mass of thermoplastic resin since less than 0.001 part by mass in some cases gives no effect while above 10 parts by mass not only gives no improvement of the effect of addition but also increases the cost.

Examples of the above-mentioned phosphorus antioxidants include: triphenyl phosphite; tris(2,4-di-tert-butylphenyl) phosphite; tris(2,5-di-tert-butylphenyl) phosphite; tris (nonylphenyl) phosphite; tris(dinonylphenyl) phosphite; tris (mono-,di-mixed nonylphenyl) phosphite; diphenyl acid phosphite; 2,2'-methylenebis(4,6-di-tert-butylphenyl)octyl phosphite; diphenyl decyl phosphite; diphenyl octyl phosphite; di(nonylphenyl)pentaerythritol diphosphite; phenyl diisodecyl phosphite; tributyl phosphite; tris(2-ethylhexyl) phosphite; tridecyl phosphite, trilauryl phosphite; dibutyl acid phosphite; dilauryl acid phosphite; trilauryl trithiophosphite; bis(neopentylglycol).1,4-cyclohexane dimethyl diphosphite; bis(2,4-di-tert-butylphenyl)pentaerythritol diphosphite; bis(2,5-di-tert-butylphenyl)pentaerythritol diphosphite; bis(2,6-di-tert-butyl-4-methylphenyl)pentaerythritol diphosphite; bis(2,4-dicumylphenyl)pentaerythritol diphosphite; distearyl pentaerythritol diphosphite; tetra (C12-15 mixed alkyl)-4,4'-isopropylidene diphenyl phosphite; bis[2,2'-methylenebis(4,6-diamylphenyl)].isopropylidene diphenyl phosphite; tetratridecyl.4,4'-butylidenebis(2-tert-butyl-5-methylphenol)diphoshite; hexa (tridecyl).1,1,3-tris(2-methyl-5-tert-butyl-4-hydroxyphenyl) butane. triphosphite; tetrakis(2,4-di-tert-butylphenyl) biphenylene diphosphonite; tris(2-[((2,4,7,9-tetrakis-tert-butyl dibenzo[d,f][1,3,2]dioxaphosphepin-6-yl)oxy]ethyl) amine; 9,10-dihydro-9-oxa-10-phosphaphenanthrene-10-oxide; 2-butyl-2-ethylpropanediol.2,4,6-tritertiary butylphenol monophosphite, and the like.

Examples of the above-mentioned phenol antioxidant include:

2,6-di-tert-butyl-p-cresol; 2,6-diphenyl-4-octadecyloxyphenol; stearyl(3,5-di-tert-butyl-4-hydroxyphenyl)propionate; distearyl (3,5-di-tert-butyl-4-hydroxybenzyl)phosphonate; tridecyl.3,5-di-tert-butyl-4-hydroxybenzyl thioacetate; thiodiethylenebis[(3,5-di-tert-butyl-4-hydroxyphenyl)propionat e]; 4,4'-thiobis(6-tert-butyl-m-cresol); 2-octylthio-4,6-di(3,5-di-tert-butyl-4-hydroxyphenoxy)-s-triazine; 2,2'-methylenebis(4-methyl-6-tert-butylphenol); bis[3,3-bis(4-hydroxy-3-tert-butylphenyl) butylic acid]glycol ester; 4,4'-butylidenebis(2,6-di-tert-butylphenol); 4,4'-butylidenebis(6-tert-butyl-3-methylphenol); 2,2'-ethylidenebis(4,6-di-tert-butylphenol); 1,1,3-tris(2-methyl-4-hydroxy-5-tertiary butylphenyl)butane; bis[2-tert-butyl-4-methyl-6-(2-hydroxy-3-teritarybutyl-5-methylbenzyl)phenyl]terephthalate; 1,3,5-tris(2,6-dimethyl-3-hydroxy-4-teritary butyl-benzyl)isocyanurate; 1,3,5-tris(3,5-di-tert-butyl-4-hydroxybenzyl)isocyanurate; 1,3,5-tris(3,5-di-tert-butyl-4-hydroxybenzyl)-2,4,6-trimethylbenzene; 1,3,5-tris[(3, 5-di-tert-butyl-4-hydroxyphenyl)propionyloxyethyl] isocyanurate; tetrakis[methylene-3-(3,5-di-tert-butyl-4-hydroxyphenyl)propionate]methane; 2-tert-butyl-4-methyl-6-(2-acryloyloxy-3-tert-butyl-5-methylbenzyl) phenol; 3,9-bis[2-(3-tert-butyl-4-hydroxy-5-methyl hydrocinnamoyloxy)-1,1-dimethylethyl]-2,4,8,10-tetraoxaspiro[5.5]undecane; triethylene glycol bis[β-(3-tert-butyl-4-hydroxy-5-methylphenyl)propionate], and the like.

Examples of the above-mentioned sulphur antioxidant include: dialkylthiodipropionates such as dilauryl ester, dimyristyl ester, myristyl stearyl ester, and distearyl ester of thiopropionic acid; and β-alkylmercaptopropionic acid esters of polyols such as pentaerythritol tetra(β-dodecylmercaptopropionate).

Examples of the above-mentionedultraviolet absorber include: 2-hydroxybenzophenones such as 2,4-dihydroxybenzophenone, 2-hydroxy-4-methoxybenzophenone, 2-hydroxy-4-octoxybenzophenone, and 5,5'-methylenebis(2-hydroxy-4-methoxybenzophenone); 2-(2-hydroxyphenyl) benzotriazoles such as 2-(2-hydroxy-5-methylphenyl) benzotriazole, 2-(2-hydroxy-5-tert-octylphenyl) benzotriazole, 2-(2-hydroxy-3,5-di-tert-butylphenyl)-5-chlorobenzotriazole, 2-(2-hydroxy-3-tert-butyl-5-methylphenyl)-5-chlorobenzotriazole, 2-(2-hydroxy-3,5-dicumylphenyl)benzotriazole, 2,2'-methylenebis(4-tert-octyl-6-benzotriazolylphenol), a polyethylene glycol ester of 2-(2-hydroxy-3-tert-butyl-5-carboxyphenyl)benzotriazole, 2-[2-hydroxy-3-(2-acryloyloxyethyl)-5-methylphenyl] benzotriazole, 2-[2-hydroxy-3-(2-metharyloyloxyethyl)-5-tert-butylphenyl]benzotriazole, 2-[2-hydroxy-3-(2-methacryloyloxyethyl)-5-tert-octylphenyl]benzotriazole, 2-[2-hydroxy-3-(2-methacryloyloxyethyl-5-tert-butylphenyl]-5-chlorobenzotriazole, 2-[(2-hydroxy-5-(2-methacryloyloxyethyl)phenyl]benzotriazole, 2-[2-hydroxy-3-tert-butyl-5-(2-methacryloyloxyethyl)phenyl]benzotriazole, 2-[2-hydroxy-3-tert-amyl-5-(2-methacryloyloxyethyl)phenyl] benzotriazole, 2-[2-hydroxy-3-tert-butyl-5-(3-methacryloyloxypropyl)phenyl]-5-chlorobenzotriazole, 2-[2-hydroxy-4-(2-methacryloyloxymethyl)phenyl]benzotriazole, 2-[2-hydroxy-4-(3-methacryloyloxy-2-hydroxypropyl)phenyl]benzotriazole, and 2-[2-hydroxy-4-(3-methacryloyloxypropyl)phenyl]benzotriazole; benzoates such as phenyl salicylate, resolsinol monobenzoate, 2,4-di-tert-butylphenyl-3,5-di-tert-butyl-4-hydroxybenzoate, hexadecyl-3,5-di-tert-butyl-4-hydroxybenzoate, and stearyl (3,5-di-tert-butyl-4-hydroxy)benzoate; substituted oxanilides such as 2-ethyl-2'-ethoxyoxanilide and 2-ethoxy-4'-dodecyloxanilide; cyanoacrylates such as ethyl-α-cyano-β,β-diphenylacrylate and methyl-2-cyano-3-methyl-3-(p-methoxyphenyl)acrylate; and metal salts or metal chelates thereof, in particular, salts or chelates of nickel or chromium thereof.

The use amount of the other additives is preferably 0.001 to 20 parts by mass, more preferably 0.01 to 1 part by mass, per 100 parts by mass of synthetic resin since less than 0.001 part by mass in some cases gives no effect while above 20 parts by mass not only gives no improvement of the effect of addition but also increases the cost.

Furthermore, the synthetic resin composition of the present invention may as necessary contain well-known general additives such as heavy metal deactivators; aluminum p-tert-butylbenzoate; dibenzylidene sorbitol; metal soaps; antistatic agents composed of nonionic surfactants, cationic surfactants, anionic surfactants, amphoteric surfactants or the like; flame retardants such as halogen (bromine, chlorine, fluorine) compounds, phosphorus compounds, metal oxides, and fluoro resins; lubricants such as ethylenebisalkyl amides; colorants such as dyes and pigments; crystallizing agents such as nucleating agents and crystallization accelerators; processing aids; inorganic additives such as hydrotalcite, talc, mica, and silica, fillers, and the like.

In the present invention, the method of adding the ultraviolet absorber represented by the above-mentioned general formula (I) and other additives optionally used to the thermoplastic resin is not particularly limited and their form upon addition may be powder, one-pack granules, suspension, emulsion or solution.

Also, the synthetic resin composition of the present invention is not particularly limited in terms of the processing method and use thereof and may be adapted to any of the usually used processing methods and uses. The processing methods include, for example, calendar processing, extrusion processing, coextrusion processing, injection molding, inflation molding, blow molding, press molding, roll processing, etc. The uses include, for example, resin parts for automobiles such as bumpers, dash-boards, and instrument panels, resin parts for household electrical appliances such as refrigerators, washing machines, and cleaners, household goods such as dinnerware, buckets, and bath products, resin parts for connection such as connectors, sundry articles such as toys, molded articles such as containers for storage and preservation, e.g., tanks, UV-cut films for construction material or decorated plates, agricultural films, optical filters for displays, various sheets, and the like.

EXAMPLES

Hereinafter, the present invention will be illustrated in more detail by production examples, examples and comparative examples. However, the present invention should not be considered as being limited by the examples and the like.

Synthesis Example

Synthesis of Intermediate Compound

In a reaction flask, 141 g of benzamidine hydrochloride and 99.0 g of phenyl resorcinate were dissolved in 580 g of ethanol and 175 g of 28 mass % methanol solution of sodium methylate was added. Methanol was evaporated at 78° C. while stirring. Furthermore, after 20 hours' stirring at 78° C., the mixture was cooled to 5° C. and the solids that deposited were filtered. The obtained solid phase was washed with methanol and with water to obtain 55.2 g (yield 38%) of an intermediate, 2-(2,4-dihydroxyphenyl)-4,6-diphenyl-1,3,5-triazine as pale yellow crystals.

In a reaction flask were charged 51.0 g of the 2-(2,4-dihydroxyphenyl)-4,6-diphenyl-1,3,5-triazine obtained as described above, 284 g of 2-bromoethanol, and 255 g of dimethylformamide and 87.6 g of an aqueous 48 mass % sodium hydroxide solution was dripped thereto, followed by reaction at 85° C. for 10 hours. After cooling the reaction mixture to 5° C., concentrated hydrochloric acid was dripped thereto at 5° C. or less to neutralize the reaction mixture to pH 7 to 6. The solid phase that deposited was filtered, washed with water and dried to obtain 46.2 g (yield 80%) of an intermediate compound, 2-[2-hydroxy-4-(2-hydroxyethyloxy)phenyl]-4,6-diphenyl-1,3,5-triazine.

Production Example 1

Synthesis of Compound No. 1

In a nitrogen-substituted reaction flask were charged 7.94 g of the intermediate compound obtained in the Synthesis Example described above, 2.58 g of cyclohexane carboxylic acid, 50 g of xylene, and 0.10 g of p-toluenesulfonic acid and the mixture was refluxed with dehydration at 140° C. for 10 hours. The resultant was washed with water until the inside system reached pH 7. After removing the solid phase by filtration, methanol was added to form crystals, which were filtered. The obtained crude crystals were recrystallized from xylene/methanol (1/3) solvent to obtain pale yellow crystals in a yield of 81%. The following analyses were made on them to confirm that the obtained crystals were identical with the objective Compound No. 1.

(1) IR analysis ($cm^{-1}$): 3440 (hydroxyl group), 2925, 2850 (cyclohexyl group), 1725 (ester group), 1535, 1510 (triazine group), 1165 (ether group).

(2) Elemental analysis (mass %): carbon; 72.3 (72.3), hydrogen; 5.61 (5.65), nitrogen; 8.71 (8.73). Note that hereinafter values in the brackets ( ) indicate theoretical values.

(3) Melting point (hereinafter, peak top by DSC analysis unless otherwise indicated specifically): 157° C.

Production Example 2

Synthesis of Compound No. 3

In a nitrogen-substituted reaction flask were charged 7.94 g of the intermediate compound obtained in the Synthesis Example described above, 3.12 g of 3-cyclohexanepropanoic acid, 50 g of xylene, and 0.10 g of p-toluenesulfonic acid and the mixture was refluxed with dehydration at 140° C. for 10 hours. The resultant was washed with water until the inside system reached pH 7. After removing the solid phase by filtration, methanol was added to form crystals, which were filtered. The obtained crude crystals were recrystallized from xylene/methanol (1/3) solvent to obtain pale yellow crystals in a yield of 83%. The following analyses were made on them to confirm that the obtained crystals were identical with the objective Compound No. 3.

(1) IR analysis ($cm^{-1}$): 3435 (hydroxyl group), 2920, 2850 (cyclohexyl group), 1728 (ester group), 1535, 1512 (triazine group), 1165 (ether group).

(2) Elemental analysis (mass %): carbon; 72.6 (72.7), hydrogen; 5.88 (5.90), nitrogen; 8.46 (8.48).

(3) Melting point: 124° C.

Production Example 3

Synthesis of Compound No. 8

In a nitrogen-substituted reaction flask were charged 7.94 g of the intermediate compound obtained in the Synthesis Example described above, 5.13 g of 2-hexyldecanoic acid, 50 g of xylene, and 0.10 g of p-toluenesulfonic acid and the mixture was refluxed with dehydration at 140° C. for 10 hours. The resultant was washed with water until the inside system reached pH 7. After removing the solid phase by filtration, methanol was added to form crystals, which were filtered. The obtained crude crystals were recrystallized from xylene/methanol (1/3) solvent to obtain pale yellow crystals in a yield of 96%. The following analyses were made on them to confirm that the obtained crystals were identical with the objective Compound No. 8.

(1) IR analysis ($cm^{-1}$): 3437 (hydroxyl group), 2924, 2855 (alkyl group), 1728 (ester group), 1535, 1510 (triazine group), 1165 (ether group).

(2) Elemental analysis (mass %): carbon; 75.0 (75.09), hydrogen; 7.90 (7.92), nitrogen; 6.71 (6.74).

(3) Melting point: 80° C.

Production Example 4

Synthesis of Compound No. 9

In a nitrogen-substituted reaction flask were charged 7.94 g of the intermediate compound obtained in the Synthesis Example described above, 5.70 g of 2-(1,3,3-trimethylbutyl)-5,7,7-trimethyloctanoic acid, 50 g of xylene, and 0.10 g of p-toluenesulfonic acid and the mixture was refluxed with dehydration at 140° C. for 10 hours. The resultant was washed with water until the inside system reached pH 7. After removing the solid phase by filtration, the solvent was removed. The obtained residue was recrystallized from xylene/methanol (1/10) solvent to obtain pale yellow crystals in a yield of 94%. The following analyses were made on them to confirm that the obtained crystal was identical with the objective Compound No. 9.
(1) IR analysis (cm$^{-1}$): 3444 (hydroxyl group), 2955, 2905, 2866 (alkyl group), 1732 (ester group), 1535, 1512 (triazine group), 1165 (ether group).
(2) Elemental analysis (mass %): carbon; 75.5 (75.54), hydrogen; 8.20 (8.19), nitrogen; 6.44 (6.45).
(3) Melting point: 71° C.

Production Example 5

Synthesis of Compound No. 11

In a nitrogen-substituted reaction flask were charged 7.94 g of the intermediate compound obtained in the Synthesis Example described above, 6.25 g of 2-octyldodecanoic acid, 50.0 g of xylene, and 0.10 g of p-toluenesulfonic acid and the mixture was refluxed with dehydration at 140° C. for 10 hours. The resultant was washed with water until the inside system reached pH 7. After removing the solid phase by filtration, the solvent was removed and the obtained residue was washed twice with methanol at 40 to 50° C. to obtain pale yellow crystals by decantation in a yield of 92%. The following analyses were made on them to confirm that the obtained solid was identical with the objective Compound No. 11.
(1) IR analysis (cm$^{-1}$): 3444 (hydroxyl group), 2958, 2928, 2870 (alkyl group), 1723 (ester group), 1537, 1515 (triazine group), 1175 (ether group).
(2) Elemental analysis (mass %): carbon; 76.0 (75.96), hydrogen; 8.42 (8.45), nitrogen; 6.16 (6.18).
(3) Melting point: 57° C.

Production Example 6

Synthesis of Compound No. 12

In a reaction flask were charged 15.0 g of the intermediate compound obtained in the Synthesis Example described above, 16.0 g of docosanoic acid, 45.0 g of xylene, and 0.60 g of p-toluenesulfonic acid and the mixture was refluxed at 140° C. for 10 hours. After the inside system was washed with water, methanol was added to form crystals, which were filtered. The obtained crude crystals were recrystallized from xylene/methanol (1/3) solvent to obtain 22.0 g of pale yellow crystals (yield of 80%). The following analyses were made on them to confirm that the obtained crystal was identical with the objective Compound No. 12.
(1) IR analysis (cm$^{-1}$): 3440 (hydroxyl group), 2920, 2845 (long-chain alkyl group), 1750 (ester group), 1160 (ether group).
2) Elemental analysis (mass %): carbon; 76.4 (76.3), hydrogen; 8.7 (8.68), nitrogen; 5.9 (5.94).
(3) Melting point: 113° C.

Production Example 7

Synthesis of Compound No. 29

In a nitrogen-substituted reaction flask were charged 8.68 g of the intermediate compound obtained in the Synthesis Example described above, 1.9 g of 1,4-cyclohexanedicarboxylic acid, 50.0 g of xylene, and 0.10 g of p-toluenesulfonic acid and the mixture was refluxed with dehydration at 140° C. for 10 hours. The resultant mixture was cooled down to room temperature to obtain the solids through filtration, which were dissolved in tetrahydrofuran into a solution, to which methanol was added to form crystals. Thus, pale yellow crystals were obtained in a yield of 62%. The following analyses were made on them to confirm that the obtained crystal was identical with the objective Compound No. 29.
(1) IR analysis (cm$^{-1}$): 3440 (hydroxyl group), 2940, 2870 (cyclohexyl group), 1723 (ester group), 1537, 1515 (triazine group), 1175 (ether group).
(2) Elemental analysis (mass %): carbon; 71.0 (71.1), hydrogen; 4.80 (4.82), nitrogen; 9.54 (9.56).
(3) Melting point measurement (visual observation): 213–215° C.

Production Example 8

Synthesis of Compound No. 32

In a nitrogen-substituted reaction flask were charged 8.68 g of the intermediate compound obtained in the Synthesis Example above, 1.9 g of 1,2-cyclohexanedicarboxylic acid, 50.0 g of xylene, and 0.10 g of p-toluenesulfonic acid and the mixture was refluxed with dehydration at 140° C. for 10 hours. The resultant was washed with water until the inside system reached pH 7. After removing the solid phase by filtration, methanol was added to form crystals, which were filtered. The obtained crude crystals were recrystallized from xylene/methanol (1/3) solvent to obtain pale yellow crystals (yield of 60%). The following analyses were made on them to confirm that the obtained crystal was identical with the objective Compound No. 32.
(1) IR analysis (cm$^{-1}$): 3437 (hydroxyl group), 2943, 2858 (cyclohexyl group), 1743 (ester group), 1531, 1510 (triazine group), 1173 (ether group).
(2) Elemental analysis (mass %): carbon; 71.0 (71.1), hydrogen; 4.80 (4.82), nitrogen; 9.54 (9.56).
(3) Melting point: 204° C.

Production Example 9

Synthesis of Compound No. 42

In a reaction flask were charged 15.0 g of the intermediate compound obtained in the Synthesis Example above, 11.0 g of hydrogenated dimer acid, 45.0 g of xylene, and 0.60 g of p-toluenesulfonic acid and the mixture was refluxed at 140° C. for 10 hours. The resultant was washed with water. Thereafter, methanol was added to form crystals, which were filtered. The obtained crude crystals were recrystal lized from xylene/methanol (1/3) solvent to obtain 23.3 g of pale yellow crystals (yield of 93%). The following analyses were made on them to confirm that the obtained crystal was identical with the objective Compound No. 42.
(1) IR analysis ($cm^{-3}$): 3440 (hydroxyl group), 2920, 2850 (alkyl group), 1740 (ester group), 1160 (ether group).
(2) Elemental analysis (mass %): carbon; 76.0 (75.8), hydrogen; 7.9 (7.91), nitrogen; 6.4 (6.47).
(3) Melting point: 87° C.

Comparative Production Example

Production of Comparative Compounds 1 to 5

By the same procedure as those in the Synthesis Examples and Production Examples described above, the following Comparative Compounds 1 to 5 were obtained from corresponding raw materials.

Comparative Compound No. 1

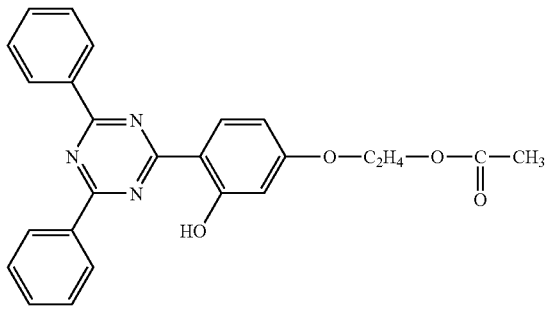

Comparative Compound No. 2

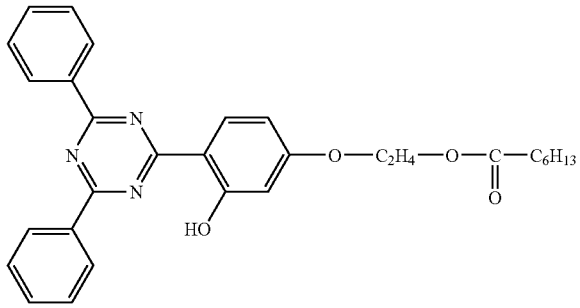

Comparative Compound No. 3

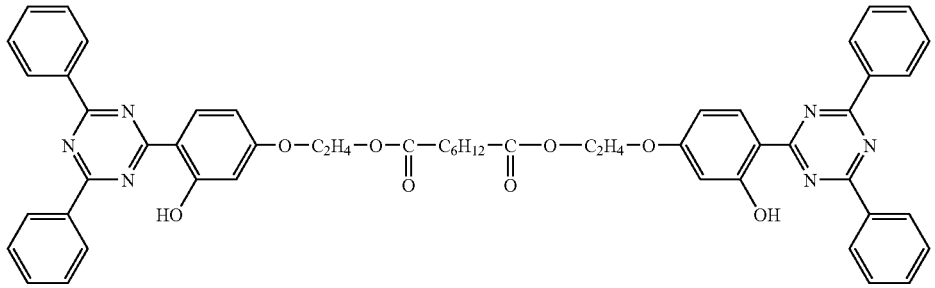

Comparative Compound No. 4

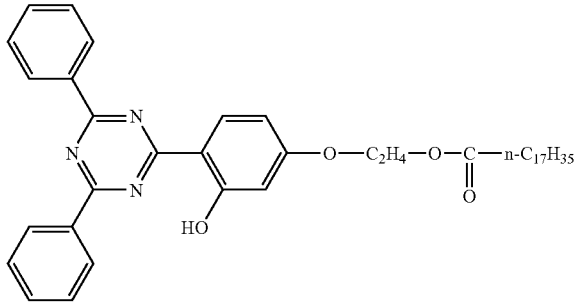

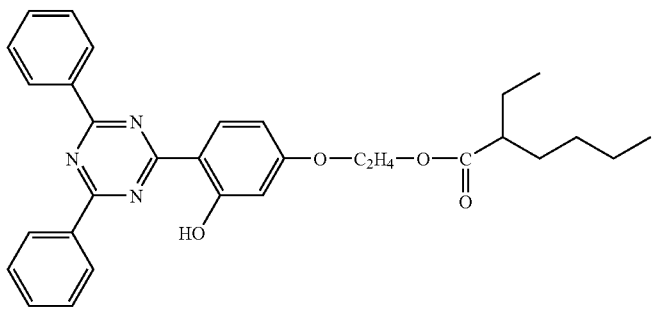

Comparative Compound No. 5

Example 1

A resin composition obtained by mixing the composition of Formulation 1 below in a mixer for 5 minutes was extruded at 280° C. at 80 rpm to obtain pellets, from which a cover layer resin composition was prepared. The cover layer resin composition and core layer resin composed of bisphenol A type polycarbonate (inherent viscosity 0.57; dioxane 30° C.) powder were simultaneously coextruded at 280° C. Immediately after the extrusion, opposing surfaces were contacted each other to prepare a sample of a two-layer structure having a core layer of 2 mm thick and a cover layer of 50 μm thick. Weathering test on this sample was performed using Sunshine Weather-O-meter under the conditions written in the margin of each table. By using a Hunter color difference meter, yellowness before the test (YI) and a difference of the yellowness (ΔY) between the yellowness after the weathering test and YI were evaluated. The results are shown in Tables 1 to 3.

| (Formulation 1) | (Unit: Part by mass) |
| --- | --- |
| Bisphenol A type polycarbonate (Inherent viscosity 0.57; dioxane 30° C.) | 100 parts by mass |
| Ultraviolet absorber (described in Tables 1 to 3.) | 10 |

Comparative Example 1

A sample compounded with no ultraviolet absorber and a sample in which a comparative compound was used as the ultraviolet absorber were prepared in the same procedure as in Example 1 and evaluations of cloudiness and weatherability thereof were made. The results are shown in Tables 1 to 3.

TABLE 1

| No. | Ultraviolet absorber | YI | ΔY |
| --- | --- | --- | --- |
| Example 1-3 | Compound No. 1 | 13.5 | 4.9 |
| Example 1-4 | Compound No. 3 | 13.0 | 4.5 |
| Example 1-5 | Compound No. 32 | 13.2 | 4.3 |
| Comparative Example 1-4 | — | 10.5 | Whitening |
| Comparative Example 1-5 | Comparative Compound 1 | 14.8 | 6.9 |
| Comparative Example 1-6 | Comparative Compound 2 | 13.6 | 6.2 |

TABLE 1-continued

| No. | Ultraviolet absorber | YI | ΔY |
| --- | --- | --- | --- |
| Comparative Example 1-7 | Comparative Compound 3 | 13.8 | 5.9, cloudy |

Black panel temperature of 83° C., Rainfall cycle of 18 minutes in 120 minutes for 1,050 hours

TABLE 2

| No. | Ultraviolet absorber | YI | ΔY |
| --- | --- | --- | --- |
| Example 1-6 | Compound No. 8 | 13.4 | 4.5 |
| Example 1-7 | Compound No. 9 | 13.3 | 4.2 |
| Example 1-8 | Compound No. 11 | 13.2 | 3.9 |
| Comparative Example 1-8 | — | 10.8 | Whitening |
| Comparative Example 1-9 | Comparative Compound 4 | 14.2 | 6.9 |

Black panel temperature of 83° C., 1,050 hours

TABLE 3

| No. | Ultraviolet absorber | YI | ΔY |
| --- | --- | --- | --- |
| Example 1-1 | Compound No. 12 | 13.5 | 5.4 |
| Example 1-2 | Compound No. 42 | 13.1 | 5.0 |
| Comparative Example 1-1 | Comparative Compound 1 | 15.8 | 7.1 |
| Comparative Example 1-2 | — | 10.8 | Whitening |
| Comparative Example 1-3 | Comparative Compound 4 | 14.2 | 6.4 |

Black panel temperature of 83° C., Rainfall cycle of 18 minutes in 120 minutes for 1,200 hours

Example 2

A resin composition obtained by mixing the composition of Formulation 2 below in a mixer for 5 minutes was extruded at 250° C. at 25 rpm to obtain pellets, which then was injection molded at 250° C. to prepare a sample of 3 mm thick. Weathering test on this sample was performed using a Xenon Weather-O-meter at a black panel temperature of 89° C. Evaluations were made on yellowness before the test (YI) and a difference of the yellowness (ΔY) between the yellowness after the weathering test for 1,500 hours and YI by using a Hunter color difference meter and on time till the occurrence of cracks (weathering time). The results are shown in Tables 4 to 8.

Comparative Example 2

A sample compounded with neither ultraviolet absorbers nor HALS, a sample compounded with no ultraviolet absorber, and a sample in which a comparative compound was used as the ultraviolet absorber were prepared in the same procedure as in Example 2 and evaluations of weatherability thereof were made in the same manner as in Example 2. The results are shown in Tables 4 to 8.

| (Formulation 2) | (Unit: Part by mass) |
|---|---|
| Ethylene/propylene block copolymer (Ethylene/propylene = 3/97, MI = 10) | 100 parts by mass |
| Calcium stearate | 0.05 |
| Stearyl (3,5-di-tert-butyl-4-hydroxyphenyl) propionate | 0.1 |
| Tris(2,4-di-tert-butylphenyl) phosphite | 0.05 |
| HALS (cf. Tables 4 to 8 below) | Tables 4 to 8 |
| Ultraviolet absorber | 0.25 |

Note that the melt index (MI) of ethylene/propylene copolymer is a value obtained at 230° C. under the condition of a load of 2.16 kg (unit g/10 minutes).

TABLE 4

HALS: Bis(2,2,6,6-tetramethyl-4-piperidyl)sebacate

| No. | HALS (Part by mass) | Ultraviolet absorber | Weathering time (Hr) | ΔY |
|---|---|---|---|---|
| Example 2-1 | 0.25 | Compound No. 3 | 3150 | 4.7 |
| Example 2-2 | 0.25 | Compound No. 32 | 3300 | 4.4 |
| Comparative Example 2-1 | — | — | Under 400 | — |
| Comparative Example 2-2 | 0.25 | — | 1400 | 10.2 |
| Comparative Example 2-3 | 0.25 | Comparative Compound 2 | 2450 | 8.6 |
| Comparative Example 2-4 | 0.25 | Comparative Compound 3 | 2800 | 7.9 |

TABLE 5

HALS: Tetrakis(1,2,2,6,6-pentamethyl-4-piperidyl)-1,2,3,4-butanetetracarboxylate

| No. | HALS (Part by mass) | Ultraviolet absorber | Weathering time (Hr) | ΔY |
|---|---|---|---|---|
| Example 2-3 | 0.25 | Compound No. 3 | 3450 | 4.6 |
| Example 2-4 | 0.25 | Compound No. 32 | 3650 | 4.2 |
| Comparative Example 2-5 | — | — | Under 400 | — |
| Comparative Example 2-6 | 0.25 | — | 1400 | 10.0 |
| Comparative Example 2-7 | 0.25 | Comparative Compound 2 | 2650 | 8.5 |
| Comparative Example 2-8 | 0.25 | Comparative Compound 3 | 2800 | 7.7 |

TABLE 6

HALS: Bis(1,2,2,6,6-pentamethyl-4-piperadyl).bis-(tridecyl)butanetetracarboxylate

| No. | HALS (Part by mass) | Ultraviolet absorber | Weathering time (Hr) | ΔY |
|---|---|---|---|---|
| Example 2-5 | 0.25 | Compound No. 3 | 3400 | 4.6 |
| Example 2-6 | 0.25 | Compound No. 32 | 3650 | 4.4 |
| Comparative Example 2-9 | — | — | Under 400 | — |
| Comparative Example 2-10 | 0.25 | — | 1500 | 10.0 |
| Comparative Example 2-11 | 0.25 | Comparative Compound 2 | 2700 | 8.6 |
| Comparative Example 2-12 | 0.25 | Comparative Compound 3 | 2900 | 7.9 |

TABLE 7

HALS: Tetrakis(2,2,6,6-tetramethyl-4-piperidyl)-1,2,3,4-butanetetracarboxylate

| No. | HALS (Part by mass) | Ultraviolet absorber | Weathering time (Hr) | ΔY |
|---|---|---|---|---|
| Example 2-7 | 0.25 | Compound No. 3 | 3400 | 4.5 |
| Example 2-8 | 0.25 | Compound No. 32 | 3550 | 4.3 |
| Comparative Example 2-13 | — | — | Under 400 | — |
| Comparative Example 2-14 | 0.25 | — | 1550 | 10.5 |
| Comparative Example 2-15 | 0.25 | Comparative Compound 2 | 2750 | 8.5 |
| Comparative Example 2-16 | 0.25 | Comparative Compound 3 | 2850 | 8.0 |

TABLE 8

HALS: 1,5,8,12-tetrakis[2,4-bis(N-butyl-N-(2,2,6,6-tetramethyl-4-piperidyl)amino)-s-triazine-6-yl]-1,5,8,12-tetraazadodecane

| No. | HALS (Part by mass) | Ultraviolet absorber | Weathering time (Hr) | ΔY |
|---|---|---|---|---|
| Example 2-9 | 0.25 | Compound No. 3 | 3200 | 4.9 |
| Example 2-10 | 0.25 | Compound No. 32 | 3400 | 4.7 |
| Comparative Example 2-17 | — | — | Under 400 | — |
| Comparative Example 2-18 | 0.25 | — | 1500 | 11.1 |
| Comparative Example 2-19 | 0.25 | Comparative Compound 2 | 2500 | 8.8 |
| Comparative Example 2-20 | 0.25 | Comparative Compound 3 | 2600 | 8.0 |

Example 3

A resin composition obtained by mixing the composition of Formulation 3 below in a mixer for 5 minutes was extruded at 250° C. at 25 rpm to obtain pellets, which then were injection-molded at 250° C. to prepare a sample having a thickness of 1 mm. The following evaluation was made. The results are shown in Table 9.

(1) Haze value (cloudiness) and total light transmittance (transparency): Samples stored at 60° C. for 30 days after the processing were measured for haze value and total light transmittance (unit: %) in accordance with JIS K7105. (In Tables, values before and after the symbol→indicate values after processing and after storage, respectively.)
(2) Initial coloring: Coloring of samples after the processing thereof was evaluated based on yellowness (YI) measured on a Hunter color difference meter.
(3) Bleed: Presence or absence of bleed was observed on samples after 30 days' storage at 60° C.

Comparative Example 3

In Formulation 3, a sample compounded with no ultraviolet absorber, and a sample in which a comparative compound was used as the ultraviolet absorber were prepared in the same procedure as in Example 3 and evaluations similar to those of Example 3 were made. The results are shown in Table 9.

| (Formulation 3) | (unit: parts by mass) |
|---|---|
| Ethylene/propylene random copolymer (ethylene/propylene = 3/97, MI = 10) | 100 parts by mass |
| Calcium stearate | 0.1 |
| Tetrakis[methylene-3-(3,5-di-tert-butyl-4-hydroxyphenyl)propionate]methane | 0.1 |
| Tris(2,4-di-tert-butylphenyl) phosphite | 0.1 |
| Ultraviolet absorber | 0.5 |

Example 4

A resin composition obtained by mixing the composition of Formulation 4 below in a mixer for 5 minutes was extruded at 250° C. at 25 rpm to obtain pellets, which then were injection-molded at 250° C. to prepare a sample having a thickness of 1 mm. The following evaluation was made. The results are shown in Table 10.
(1) Haze value (cloudiness) and total light transmittance (transparency): Measurements were performed in the same manner as in Example 3.
(2) Weathering tests: Weathering tests were performed by using a Sunshine Weather-O-meter at a black panel temperature of 83° C. Evaluations were made on yellowness before the test (YI) and a difference of the yellowness ($\Delta Y$) between the yellowness after the weathering test for 1,050 hours and YI, and on time till the occurrence of cracks (weathering time).

Comparative Example 4

In Formulation 4, a sample compounded with no ultraviolet absorber was prepared in the same procedure as in Example 4 and evaluations similar to those of Example 4 were made. The results are shown in Table 10.

| (Formulation 4) | (unit: parts by mass) |
|---|---|
| Ethylene/propylene random copolymer (ethylene/propylene = 3/97, MI = 10) | 100 parts by mass |
| Calcium stearate | 0.1 |
| Tetrakis[methylene-3-(3,5-di-tert-butyl-4-hydroxyphenyl)propionate]methane | 0.1 |
| Tris(2,4-di-tert-butylphenyl) phosphite | 0.1 |
| Ultraviolet absorber; Compound No. 11 | 0.5 |
| HALS | 0.2 |

TABLE 9

| No. | Ultraviolet absorber | Haze value | Light transmittance | Initial coloring | Bleed |
|---|---|---|---|---|---|
| Example 3-1 | Compound No. 8 | 48.4→51.3 | 97.1→91.0 | 3.6 | Absence |
| Example 3-2 | Compound No. 9 | 49.6→52.6 | 92.2→92.0 | 3.6 | Absence |
| Example 3-3 | Compound No. 11 | 47.1→51.0 | 91.0→90.9 | 3.4 | Absence |
| Comparative Example 3-1 | — | 42.3→45.3 | 93.6→93.5 | 3.2 | Absence |
| Comparative Example 3-2 | Comparative Compound 4 | 56.1→59.0 | 88.8→88.2 | 4.7 | Minuteness |
| Comparative Example 3-3 | Comparative Compound 5 | 62.4→66.7 | 81.2→79.4 | 4.0 | Presence |

TABLE 10

| No. | HALS | Haze value | Light transmittance | Weathering time (Hr) | YI | ΔY |
|---|---|---|---|---|---|---|
| Example 4-1 | ADEKA STAB LA-62*1 | 48.6→51.6 | 90.2→89.9 | 3100 | 3.8 | 2.6 |
| Example 4-2 | ADEKA STAB LA-63*2 | 48.4→51.9 | 90.4→90.2 | 3100 | 3.8 | 2.8 |
| Example 4-3 | CHINUBIN 944*3 | 48.8→52.4 | 90.1→89.9 | 3000 | 3.6 | 3.4 |
| Comparative Example 4-1 | ADEKA STAB LA-62 (No UVA) | 47.6→51.5 | 92.9→92.6 | 1250 | 3.6 | 12.4 |
| Comparative Example 4-2 | ADEKA STAB LA-63 (No UVA) | 47.4→51.4 | 92.9→92.8 | 1300 | 3.6 | 12.3 |
| Comparative Example 4-3 | CHINUBIN 944 (No UVA) | 47.9→52.0 | 92.7→92.5 | 1200 | 3.6 | 13.0 |

*1 Produced by Asahi Denka Kogyo K.K.; bis(1,2,2,6,6-pentamethyl-4-piperidyl).bis(tridecyl)-1,2,3,4-butanetetracarboxylate
*2 Produced by Asahi Denka Kogyo K.K.; 3,9-bis[1,1-dimethyl-2-{tris(1,2,2,6,6-pentamethyl-4-piperidyloxycarbonyloxy)butylcarbonyloxy}ethyl]-2,4,8,10-tetraoxaspiro[5.5]undecane
*3 Produced by Chiba Speciality Chemicals Inc.; 1,6-bis(2,2,6,6,-tetramethyl-4-piperidylamino)hexane/2,4-dichloro-6-tert-octylamino-s-triazine polycondensate Example 5

A resin composition obtained by mixing the composition of Formulation 5 below in a mixer for 5 minutes was extruded at 250° C. at 25 rpm to obtain pellets, which then were injection-molded at 250° C. to prepare a sample having a thickness of 2 mm. Weathering test on this sample was performed using a Sunshine Weather-O-meter at a black panel temperature of 83° C. in a rainfall cycle of 18 minutes in 120 minutes. Evaluations were made on the yellowness, 500 hours and 1,500 hours after the start of the test by using a Hunter color difference meter, and on time till the occurrence of cracks (weathering time) The results are shown in Tables 11 to 15.

| (Formulation 5) | (unit: parts by mass) |
|---|---|
| Ethylene/propylene copolymer | 100 parts by mass |
| Calcium stearate | 0.05 |
| Stearyl (3,5-di-tert-butyl-4-hydroxyphenyl) propionate | 0.1 |
| Tris(2,4-di-tert-butylphenyl) phosphite | 0.05 |
| HALS | Table 11 to Table 15 |
| Ultraviolet absorber | 0.3 |

TABLE 11

HALS: Bis(2,2,6,6-tetramethyl-4-piperidyl)sebacate

| NO. | HALS (Part by mass) | Ultraviolet absorber | Weathering time (Hr) | Yellowness 500 Hours | Yellowness 1500 Hours |
|---|---|---|---|---|---|
| Example 5-1 | 0.3 | Compound No. 12 | 3300 | 4.0 | 6.9 |
| Example 5-2 | 0.3 | Compound No. 42 | 3400 | 3.8 | 6.5 |
| Comparative Example 5-1 | 0.3 | Comparative Compound 1 | 2400 | 5.0 | 13.4 |
| Comparative Example 5-2 | 0 | — | 400 | 13.0 | black |
| Comparative Example 5-3 | 0.3 | — | 1500 | 9.2 | 17.1 |

TABLE 12

HALS: Tetrakis(1,2,2,6,6-pentamethyl-4-piperidyl)-1,2,3,4-butanetetracarboxylate

| NO. | HALS (Part by mass) | Ultraviolet absorber | Weathering time (Hr) | Yellowness 500 Hours | Yellowness 1500 Hours |
|---|---|---|---|---|---|
| Example 5-3 | 0.3 | Compound No. 12 | 3700 | 3.8 | 6.4 |
| Example 5-4 | 0.3 | Compound No. 42 | 3800 | 3.6 | 6.1 |
| Comparative Example 5-4 | 0.3 | Comparative Compound 1 | 2700 | 4.7 | 11.6 |
| Comparative Example 5-5 | 0.3 | — | 1700 | 8.8 | 16.5 |

TABLE 13

HALS:
Bis(1,2,2,6,6-pentamethyl-4-piperidyl).bis(tridecyl)butanetetracarboxylate

| NO. | HALS (Part by mass) | Ultraviolet absorber | Weathering time (Hr) | Yellowness 500 Hours | Yellowness 1500 Hours |
|---|---|---|---|---|---|
| Example 5-5 | 0.3 | Compound No. 12 | 3700 | 4.4 | 6.8 |
| Example 5-6 | 0.3 | Compound No. 42 | 3800 | 4.2 | 6.5 |
| Comparative Example 5-6 | 0.3 | Comparative Compound 1 | 2500 | 5.3 | 13.1 |
| Comparative Example 5-7 | 0.3 | — | 1600 | 9.6 | 17.0 |

TABLE 14

HALS:
Tetrakis(2,2,6,6-tetramethyl-4-piperidyl)-1,2,3,4-butanetetracarboxylate

| NO. | HALS (Part by mass) | Ultraviolet absorber | Weathering time (Hr) | Yellowness 500 Hours | Yellowness 1500 Hours |
|---|---|---|---|---|---|
| Example 5-7 | 0.3 | Compound No. 12 | 3700 | 4.2 | 6.6 |
| Example 5-8 | 0.3 | Compound No. 42 | 3700 | 4.0 | 6.2 |
| Comparative Example 5-8 | 0.3 | Comparative Compound 1 | 2600 | 5.0 | 11.9 |
| Comparative Example 5-9 | 0.3 | — | 1600 | 9.2 | 17.2 |

TABLE 15

HALS:
1,5,8,12-tetrakis[2,4-bis(N-butyl-N-(2,2,6,6-tetramethyl-4-piperidyl)amino)-s-triazine-6-yl]-1,5,8,12-tetraazadodecane

| NO. | HALS (Part by mass) | Ultraviolet absorber | Weathering time (Hr) | Yellowness 500 Hours | Yellowness 1500 Hours |
|---|---|---|---|---|---|
| Example 5-9 | 0.3 | Compound No. 12 | 3400 | 4.3 | 7.2 |
| Example 5-10 | 0.3 | Compound No. 42 | 3600 | 4.0 | 7.0 |
| Comparative Example 5-10 | 0.3 | Comparative Compound 1 | 2400 | 4.9 | 12.7 |
| Comparative Example 5-11 | 0.3 | — | 1500 | 9.0 | 17.4 |

Example 6

A resin composition obtained by mixing the composition of Formulation 6 below in a mixer for 5 minutes was extruded at 250° C. at 25 rpm to obtain pellets, which then were injection-molded at 250° C. to prepare a sample having a thickness of 2 mm. Weathering test on this sample was performed using a Sunshine Weather-O-meter at a black panel temperature of 83° C. in a rainfall cycle of 18 minutes in 120 minutes. Evaluations were made on the yellowness, 500 hours and 1,500 hours after the start of the test by using a Hunter color difference meter, and on time till the occurrence of cracks (weathering time) The results are shown in Tables 16.

| (Formulation 6) | (unit: parts by mass) |
|---|---|
| Polypropylene (PROFAX 6501; produced by Montell, Inc.) | 100 parts by mass |
| Calcium stearate | 0.05 |
| Tetrakis[methylene-3-(3,5-di-tert-butyl-4-hydroxyphenyl)propionate]methane | 0.1 |
| Tris(2,4-di-tert-butylphenyl) phosphite | 0.1 |
| HALS: 3,9-bis[1,1-dimethyl-2-{tris(1,2,2,6,6-pentamethyl-4-piperidyloxycarbonyloxy)-butylcarbonyloxy}ethyl]-2,4,8,10-tetraoxaspiro[5.5]undecane | Table 16 |
| Ultraviolet absorber | 0.3 |

TABLE 16

| NO. | HALS (Part by mass) | Ultraviolet absorber | Weathering time (Hr) | Yellowness 500 Hours | Yellowness 1500 Hours |
|---|---|---|---|---|---|
| Example 6-1 | 0.3 | Compound No. 12 | 3500 | 4.0 | 7.2 |
| Example 6-2 | 0.3 | Compound No. 14 | 3500 | 3.9 | 7.4 |
| Example 6-3 | 0.3 | Compound No. 16 | 3500 | 4.0 | 7.0 |
| Example 6-4 | 0.3 | Compound No. 42 | 3700 | 3.8 | 6.9 |
| Comparative Example 6-1 | 0.3 | Comparative Compound 1 | 2300 | 5.5 | 15.5 |
| Comparative Example 6-2 | 0.3 | Comparative Compound 4 | 3200 | 4.3 | 7.7 |
| Comparative Example 6-3 | 0.3 | — | 1400 | 11.0 | 21.0 |

Example 7

A resin composition obtained by mixing the composition of Formulation 7 below in a mixer for 5 minutes was extruded at 240° C. at 25 rpm to obtain pellets, which then were injection-molded at 240° C. to prepare a sample having a thickness of 2 mm. Weathering test on this sample was performed using a Sunshine Weather-O-meter at a black panel temperature of 83° C. in a rainfall cycle of 18 minutes in 120 minutes. Evaluations were made on the yellowness, 500 hours and 1,500 hours after the start of the test by using a Hunter color difference meter, and on time till the occurrence of cracks (weathering time). The results are shown in Tables 17.

| (Formulation 7) | (unit: parts by mass) |
|---|---|
| High-density polyethylene (HI-ZEX; produced by Mitsui Chemicals, Inc.) | 100 parts by mass |
| Calcium stearate | 0.05 |
| Tetrakis[methylene-3-(3,5-di-tert-butyl-4-hydroxyphenyl)propionate]methane | 0.1 |
| Distearyl thiodipropionate | 0.05 |
| HALS: bis(2,2,6,6-tetramethyl-4-piperidyl) sebacate | Table 8 |
| Ultraviolet absorber | 0.3 |

TABLE 17

| NO. | HALS (Part by mass) | Ultraviolet absorber | Weathering time (Hr) | Yellowness 500 Hours | Yellowness 1500 Hours |
|---|---|---|---|---|---|
| Example 7-1 | 0.3 | Compound No. 12 | 3900 | 3.9 | 5.8 |
| Example 7-2 | 0.3 | Compound No. 42 | 4100 | 3.6 | 5.5 |
| Comparative Example 7-1 | 0.3 | Comparative Compound 1 | 2900 | 4.3 | 10.4 |
| Comparative Example 7-2 | 0.3 | Comparative Compound 4 | 3400 | 4.5 | 10.8 |
| Comparative Example 7-3 | 0.3 | — | 1800 | 7.4 | 14.1 |

Example 8

A resin composition obtained by mixing the composition of Formulation 8 below in a mixer for 5 minutes was extruded at 300° C. at 50 rpm to obtain pellets, which then were injection-molded at 305° C. to prepare a sample having a thickness of 2 mm. Weathering test on this sample was performed using a Sunshine-O-meter at a black panel temperature of 83° C. for 1200 hours in a rainfall cycle of 18 minutes in 120 minutes. By using a Hunter color difference meter, a difference (ΔY) between the yellowness before the test and the yellowness after the weathering test was evaluated. The results are shown in Table 18.

Comparative Example 8

A sample compounded with no ultraviolet absorber, and a sample in which a comparative compound was used as the ultraviolet absorber were prepared in the same procedure as in Example 8 and evaluations of weatherability thereof were made as in Example 8. The results are shown in Table 18.

| (Formulation 8) | (unit: parts by mass) |
|---|---|
| Polyethylene terephthalate (NOVAPET 6010G30; produced by Mitsubishi Engineering Plastics K.K.) | 100 parts by mass |
| Ultraviolet absorber | 0.5 |

TABLE 18

| No. | Ultraviolet absorber | ΔY |
|---|---|---|
| Example 8-1 | Compound No. 3 | 2.1 |
| Example 8-2 | Compound No. 29 | 2.0 |
| Example 8-3 | Compound No. 32 | 1.8 |
| Comparative Example 8-1 | — | Whitening |
| Comparative Example 8-2 | Comparative Compound 2 | 3.6 |
| Comparative Example 8-3 | Comparative Compound 3 | 3.8 |

Example 9

A resin composition obtained by mixing the composition of Formulation 9 below in a mixer for 5 minutes was extruded at 300° C. at 50 rpm to obtain pellets, which then were injection-molded at 305° C. to prepare a sample having a thickness of 2 mm. The same evaluation as Example 9 was made. The results are shown in Table 19.

Comparative Example 9

A sample compounded with no ultraviolet absorber, and a sample in which a comparative compound was used as the ultraviolet absorber were prepared in the same procedure as in Example 9 and evaluations of weatherability thereof were made as in Example 9. The results are shown in Table 19.

| (Formulation 9) | (unit: parts by mass) |
|---|---|
| Polybutylene terephthalate (NOVADURAN 5010R5; produced by Mitsubishi Engineering Plastics K.K.) | 100 parts by mass |
| Decabromodiphenyl oxide | 0.1 |
| Ultraviolet absorber | 0.5 |

TABLE 19

| No. | Ultraviolet absorber | ΔY |
|---|---|---|
| Example 9-1 | Compound No. 3 | 2.5 |
| Example 9-2 | Compound No. 29 | 2.3 |
| Example 9-3 | Compound No. 32 | 2.2 |
| Comparative Example 9-1 | — | Whitening |
| Comparative Example 9-2 | Comparative Compound 2 | 4.0 |
| Comparative Example 9-3 | Comparative Compound 3 | 3.5 |

Example 10

A resin composition obtained by mixing a composition comprising 100 parts by mass of a resin component, 0.3 part by mass of HALS: tetrakis(1,2,2,6,6-pentamethyl-4-piperidyl)-1,2,3,4-butanetetracarboxylate, 0.3 part by mass of the ultraviolet absorber described in Table 20 in a mixer for 5 minutes was extruded into pellets at 25 rpm and injection molded to prepare samples of 2 mm thick. The processing temperatures of pellets and samples are shown in Table 20. The samples were subjected to weathering tests by using a Sunshine Weather-O-meter at a black panel temperature of 83° C. without rainfall. Evaluations were made on the difference ΔY between the yellowness before the test and the yellowness after 1,200 hours. The results are shown in Table 20.

Comparative Example 10

A sample in which a comparative compound was used as the ultraviolet absorber was prepared in the same procedure as in Example 10 and evaluations of weatherability thereof were made as in Example 10. The results are shown in Table 20.

TABLE 20

| No. | Synthetic resins | Ultraviolet absorber | Processing temperatures of pellets (° C.) | Processing temperatures of samples (° C.) | Difference in the yellowness (ΔY) |
|---|---|---|---|---|---|
| Example 10-1 | ABS | Compound No. 1 | 230 | 230 | 2.0 |
| Example 10-2 | ABS | Compound No. 42 | 230 | 230 | 2.2 |
| Comparative Example 10-1 | ABS | Comparative Compound 1 | 230 | 230 | 3.2 |
| Comparative Example 10-2 | ABS | Comparative Compound 2 | 230 | 230 | 3.1 |
| Example 10-3 | PPO | Compound No. 3 | 300 | 300 | 1.9 |
| Example 10-4 | PPO | Compound No. 42 | 300 | 300 | 2.0 |
| Comparative Example 10-3 | PPO | Comparative Compound 1 | 300 | 300 | 2.9 |
| Comparative Example 10-4 | PPO | Comparative Compound 2 | 300 | 300 | 2.8 |
| Example 10-5 | Nylon 6 | Compound No. 29 | 250 | 240 | 2.0 |
| Example 10-6 | Nylon 6 | Compound No. 42 | 250 | 240 | 2.1 |
| Comparative Example 10-5 | Nylon 6 | Comparative Compound 1 | 250 | 240 | 3.0 |
| Comparative Example 10-6 | Nylon 6 | Comparative Compound 3 | 250 | 240 | 2.8 |
| Example 10-7 | PMMA | Compound No. 32 | 220 | 220 | 1.8 |
| Example 10-8 | PMMA | Compound No. 42 | 220 | 220 | 1.9 |
| Comparative Example 10-7 | PMMA | Comparative Compound 1 | 220 | 220 | 2.8 |
| Comparative Example 10-8 | PMMA | Comparative Compound 3 | 220 | 220 | 2.9 |

ABS: STYRAK 100; produced by Asahikasei Corporation
PPO: ZYLON 500H; produced by Asahikasei Corporation
Nylon 6: NOVAMID 1020A7; produced by Mitsubishi Engineering Plastics K.K.
PMMA: DELPET 60N; produced by Asahikasei Corporation

INDUSTRIAL APPLICABILITY

According to the present invention, an ultraviolet absorber composed of a triazine compound that has good compatibility and/or dispersibility with a resin component and provides sufficient effects of addition can be obtained. Use of this can give rise to a synthetic resin composition for molded articles having improved weatherability, cloudness, blooming, etc.

The invention claimed is:

1. An ultraviolet absorber for synthetic resins, comprising a triazine compound represented by general formula (I) shown below

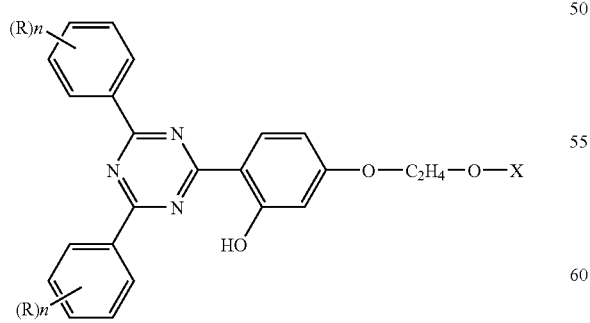

(I)

wherein (R represents an alkyl group having 1 to 4 carbon atoms, n is 0 or an integer of up to 2, and X represents a group selected from the group consisting of (a) and (d) below:

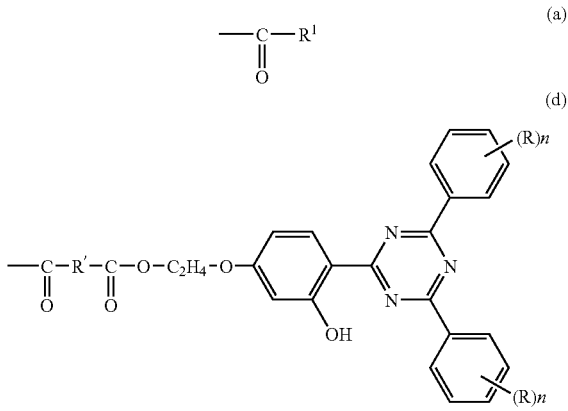

wherein ($R^1$ represents an aliphatic group having 5 to 60 carbon atoms, which is a group selected from the group consisting of an alicyclic group and an alkyl group having an alicyclic group at the terminal or in the chain thereof, when the aliphatic group has 5 to 8 carbon atoms;

a group selected from the group consisting of an alicyclic group, and an alkyl group having an alicyclic group at the terminal or in the chain thereof, when the aliphatic group has 9 to 19 carbon atoms; or a group selected from the group consisting of an alicyclic group, and an alkyl group having an alicyclic group at the terminal or in the chain thereof, when the aliphatic group has 20 to 60 carbon atoms;

R' represents an aliphatic diyl group having 5 to 60 carbon atoms, which is a group selected from the group consisting of an alicyclic group and an alkanediyl group having an alicyclic group at the terminal or in the chain thereof, when the aliphatic group has 5 to 8 carbon atoms;

a group selected from the group consisting of an alicyclic group, and an alkanediyl group having an alicyclic group at the terminal or in the chain thereof, when the aliphatic group has 9 to 19 carbon atoms; or a group selected from the group consisting of an alicyclic group, and an alkanediyl group having an alicyclic group at the terminal or in the chain thereof, when the aliphatic group has 20 to 60 carbon atoms;

R and n have the same meaning as those described in the general formula (I).

2. An ultraviolet absorber for synthetic resins according to claim 1, wherein in the general formula (I), X is a group represented by (a) or (d).

3. An ultraviolet absorber for synthetic resins according to claim 1, wherein in the general formula (I), and in the group represented by X in the general formula (I), n is 0.

4. A synthetic resin composition comprising 100 parts by mass of a synthetic resin having compounded therein 0.001 to 25 parts by mass of the ultraviolet absorber for synthetic resins according to claim 1.

5. A synthetic resin composition according to claim 4, further containing 0.001 to 10 parts by mass of at least one hindered amine light stabilizer.

6. A synthetic resin composition according to claim 4, wherein the synthetic resin is selected from polycarbonate resins, polyolefin resins and polyester resins.

* * * * *